United States Patent
Theologou et al.

(10) Patent No.: US 10,324,229 B2
(45) Date of Patent: Jun. 18, 2019

(54) SYSTEM AND METHOD OF PORE TYPE CLASSIFICATION FOR PETROPHYSICAL ROCK TYPING

(71) Applicant: Chevron U.S.A. Inc., San Ramon, CA (US)

(72) Inventors: Paul Theologou, Houston, TX (US); Mark Skalinski, Houston, TX (US); Robert K. Mallan, Houston, TX (US)

(73) Assignee: CHEVRON U.S.A. INC., San Ramon, CA (US)

( * ) Notice: Subject to any disclaimer, the term of this patent is extended or adjusted under 35 U.S.C. 154(b) by 637 days.

(21) Appl. No.: 14/919,890

(22) Filed: Oct. 22, 2015

(65) Prior Publication Data
US 2016/0124115 A1    May 5, 2016

Related U.S. Application Data

(60) Provisional application No. 62/067,745, filed on Oct. 23, 2014, provisional application No. 62/159,678, filed on May 11, 2015.

(51) Int. Cl.
*G01V 99/00* (2009.01)
*G01N 15/08* (2006.01)
*G01N 33/24* (2006.01)

(52) U.S. Cl.
CPC ....... *G01V 99/005* (2013.01); *G01N 15/0886* (2013.01); *G01N 33/241* (2013.01);
(Continued)

(58) Field of Classification Search
CPC ...... G01V 99/00; G01V 99/005; G01N 15/08; G01N 15/0886; G01N 33/241; G01N 2223/649; G01N 2015/0813
(Continued)

(56) References Cited

U.S. PATENT DOCUMENTS 6,823,298 B1 * 11/2004 Jones ................. G01N 33/2823
703/10
9,097,821 B2   8/2015 Skalinski et al.
(Continued)

FOREIGN PATENT DOCUMENTS

WO    WO 2013/10631 A1 *  7/2013

OTHER PUBLICATIONS

Nooruddin et al. Using soft computing techniques to predict corrected air permeability using Thomeer parameters, air porosity and grain density, 2013.*
(Continued)

*Primary Examiner* — Sujoy K Kundu
*Assistant Examiner* — Lynda Dinh

(57) ABSTRACT

Embodiments of a method of pore type classification for petrophysical rock typing are disclosed herein. In general, embodiments of the method utilize parameterization of MICP data and/or other petrophysical data for pore type classification. Furthermore, embodiments of the method involve extrapolating, predicting, or propagating the pore type classification to the well log domain. The methods described here are unique in that: they describe the process from sample selection through log-scale prediction; PTGs are defined independently of the original depositional geology; parameters which describe the whole MICP curve shape can be utilized; and objective clustering can be used to remove subjective decisions. In addition, the method exploits the link between MICP data and the petrophysical characteristics of rock samples to derive self-consistent predictions of PTG, porosity, permeability and water saturation.

18 Claims, 17 Drawing Sheets

(52) U.S. Cl.
CPC ............... *G01N 2015/0813* (2013.01); *G01N 2223/649* (2013.01)

(58) Field of Classification Search
USPC ........................................................ 702/11
See application file for complete search history.

(56) References Cited

U.S. PATENT DOCUMENTS

| | | | | |
|---|---|---|---|---|
| 2009/0105956 | A1* | 4/2009 | Goswami | G01V 1/48 702/11 |
| 2010/0010744 | A1* | 1/2010 | Prange | G01V 3/32 702/7 |
| 2012/0065888 | A1* | 3/2012 | Wu | G01V 3/32 702/8 |
| 2012/0221306 | A1* | 8/2012 | Hurley | G01V 99/005 703/6 |
| 2012/0275658 | A1* | 11/2012 | Hurley | G06T 7/0004 382/109 |
| 2013/0179080 | A1 | 7/2013 | Skalinski et al. | |
| 2014/0257702 | A1* | 9/2014 | Al-Ibrahim | G01V 9/02 702/7 |

OTHER PUBLICATIONS

Dernaika et al; Whole core vs. plugs: Integrating log and core data to decrease uncertainty in petrophysical interpretation and oil-in-place calculations; 2011.*

Xu, Chicheng, et al.; "Multi-Scale Orthogonal Rock Class Decomposition: Top-Down Reservoir Characterization Integrating Logs and Core in Tight Gas Sands"; SPWLA 54th Annual Logging Symposium, Jun. 2013, pp. 1-16.

Xu, Chicheng, et al.; "Pore System Characterization and Petrophysical Rock Classification Using a Bimodal Gaussian Density Function"; Jul. 2013, Math. Geosci., vol. 45, No. 6, pp. 753-771.

International Search Report, dated Feb. 5, 2016, during the prosecution of International Application No. PCT/US2015/056880.

Written Opinion of the International Searching Authority, dated Feb. 5, 2016, during the prosecution of International Application No. PCT/US2015/056880.

Al-Aruri, Ahmad, et al.; "Rock Type and Permeability Prediction from Mercury Injection Data: Application to a Heterogeneous Carbonate Oil Reservoir, Offshore Abu Dhabi (UAE)"; Oct. 1998, SPE 49556, pp. 319-343.

Clerke, Edward A., et al.; "Application of Thomeer Hyperbolas to Decode the Pore Systems, Facies and Reservoir Properties of the Upper Jurassic Arab D Limestone, Ghawar Field, Saudi Arabia: A "Rosetta Stone" Approach"; GeoArabia, 2008, vol. 13, No. 4, pp. 113-160.

Robinson, Robert B.; "Classification of Reservoir Rocks by Surface Texture"; Bulletin of the American Associate of Petroleum Geologists, vol. 50, No. 3, Mar. 1966, pp. 547-559.

Skelt, Christopher, et al.; "An Integrated Approach to Saturation Height Analysis"; SPWLA 36th Annual Logging Symposium, Jun. 1995, Paper NNN, pp. 1-10.

Thomeer, J.H.M.; "Introduction of a Pore Geometrical Factor Defined by the Capillary Pressure Curve"; Mar. 1960, 34th Annual Fall Meeting of SPE, Paper 1324-G, pp. 73-77.

Xu, Chicheng, et al.; "Petrophysical Rock Classification in the Cotton Valley Tight-Gas Sandstone Reservoir with a Clustering Pore-System Orthogonality Matrix"; Interpretation, vol. 2, No. 1, Feb. 2014, pp. T-13-T-23.

Alhanai, Waddah; "Use of Pore-Size Distributions from Mercury Injection to Derive Correlations Between Pore-Size Population Statistics and Rock/Flor Parameters"; Poster, SCA-Poster, University of Stavanger, Norway, date/page numbers not provided.

Buiting, J.M., et al.; "Permeability from Porosimetry Measurements: Derivation for a Tortuous and Fractal Tubular Bundle"; Journal of Petroleum Science and Engineering, 2013, vol. 108, pp. 267-278.

Clerke, Edward A., et al; "Application of Thomeer Hyperbolas to Decode the Pore Systems, Facies and Reservoir Properties of the Upper Jurassic Arab D Limestone, Ghawar Field, Saudi Arabia: A "Rosetta Stone" Approach"; GeoArabia, vol. 13, No. 4, 2008, pp. 113-160.

Clerke, Edward A.; "Permeability, Relative Permeability, Microscopic Displacement Efficiency, and Pore Geometry of M_1 Bimodal Pore Systems in Arab D Limestone"; Sep. 2009, SPE Journal, pp. 524-531.

Clerke, E.A., et al.; "Wireline Spectral Porosity Analysis of the Arab Limestone—From Rosetta Stone to Cipher"; SPWLA 55th Annual Logging Symposium, May 2014, pp. 1-23.

Corbett, Patrick W.M., et al.; "Estimating the Mean Permeability: How Many Measurements Do You Need?"; First Break, vol. 10, No. 3, Mar. 1992, pp. 89-94.

Gao, Bo, et al.; "New Method for Predicting Capillary Pressure Curves from NMR Data in Carbonate Rocks"; SPWLA 52nd Annual Logging Symposium, May 2011, pp. 1-10.

Gueguen, Yves, et al.; "Introduction to the Physics of Rocks"; Title pages, Table of Contents page, Preface page, Chapter 2 (Porous Media), p. 33-34, 1994.

"Histogram Interpretation: Bimodal Mixture of 2 Normals"; EDA Techniques, Engineering Statistics Handbook, Apr. 2012, Section 1.3.3.14.5, downloaded on Jan. 27, 2016: http://www.itl.nist.gov/div898/handbook/eda/section3/histogr5.htm, 2 pages, Engineering Statistics Handbook, Apr. 2012.

Huang, David D., et al. "An Improved Model for Relative Permeability and Capillary Pressure Incorporating Wettability"; SCA-9718, Sep. 1997, presented at the SCA International Symposium, Calgary, Canada, no page numbers.

Kodesova, Radka; "Percolation Theory and its Application for Interpretation of Soil Water Retention Curves"; Lecture given at the College of Soil Physics, Mar. 2003, no page numbers.

Kolodzie, Stanley, Jr.; "Analysis of Pore Throat Size and Use of the Waxman-Smits Equation to Determine Ooip in Spindle Field, Colorado"; SPE 9382, 55th Annual Fall Technical Conference and Exhibition of the Society of Petroleum Engineers of AIME, Sep. 1980, pp. 1-4 (with 10 figures).

Marzouk, I., et al.; "New Classification of Carbonate Rocks for Reservoir Characterization"; SPE 49475, 8th Abu Dhabi International Petroleum Exhibition and Conference held in Abu Dhabi, U.A.E., Oct. 1998, pp. 178-187.

Purcell, W.R.; "Capillary Pressures—Their Measurement Using Mercury and the Calculation of Permeability Therefrom"; T.P. 2544, Petroleum Transactions, AIME, Feb. 1949, pp. 39-48.

Rice University, Chapter 3 Rock Properties, downloaded on Jan. 26, 2016: http://www.owlnet.rice.edu/~ceng571/notes.htm, date/page numbers not provided (59 pages), last updated on Dec. 20, 2000, page maintained by: G. J. Hiraski, gih@rice.edu.

Robinson, Robert B.; "Classification of Reservoir Rocks by Surface Texture"; Bulletin of the American Association of Petroleum Geologists, vol. 50, No. 3, pp. 547-559, 14 Figs, 2 Tables, Mar. 1966.

Saneifar, Mehrnoosh, et al.; "Integrated Petrophysical Rock Classification in the McElroy Field, West Texas, USA"; Petrophysics, vol. 56, No. 5, Oct. 2015, pp. 493-210 (21 Figs, 3 Tables).

Shafer, John, et al.; "Mercury Porosimetry Protocol for Rapid Determination of Petrophysical and Reservoir Quality Properties"; International Symposium of the Society of Core Analysts; SCA paper No. 2021, no page numbers.

Skalinski, Mark, et al.; "Carbonate Petrophysical Rock Typing: Integrating Geological Attributes and Petrophysical Properties While Linking With Dynamic Behaviour"; Fundamental Controls on Fluid Flow in Carbonates, Current Workflows to Emerging Technologies From S.M. Agar and S. Geiger (eds) 2015, Geological Society, London, Special Publications 406, title pages and pp. 229-259.

Swanson, B.F.; "A Simple Correlation Between Permeabilities and Mercury Capillary Pressures"; Journal of Petroleum Technology, 1981, pp. 2498-2504.

Theologou, Paul N., et al.; "An MICP-Based Pore Typing Workflow—Core Scale to Log Scale"; SPWLA 56th Annual Logging Symposium, Jul. 2015; pp. 1-6.

(56) References Cited

OTHER PUBLICATIONS

Wu, Kejian, et al.; "Investigation of the Impact of Diagenesis on the Petrophysical Properties in the Complex Porosity Systems in Carbonates"; SPWLA 54$^{th}$ Annual Logging Symposium, Jun. 2013, pp. 1-13.

Xu, Chicheng, et al.; "Petrophysical Rock Classification in the Cotton Valley Tight-Gas Sandstone Reservoir with a Clustering Pore-System Orthogonality Matrix"; Technical Paper, Interpretation vol. 2, No. 1, Feb. 2014, pp. T13-T23 (17 Figs, 2 Tables).

Ye, Shin-Ju, et al.; "A New Tool for Electro-Facies Analysis: Multi-Resolution Graph-Based Clustering"; SPWLA 41$^{st}$ Annual Logging Symposium, Jun. 2000, pp. 1-14.

\* cited by examiner (a)

(b)

US 10,324,229 B2

SYSTEM AND METHOD OF PORE TYPE CLASSIFICATION FOR PETROPHYSICAL ROCK TYPING

CROSS-REFERENCE TO RELATED APPLICATIONS

The present application claims priority from U.S. Provisional Patent Application No. 62/067,745, filed Oct. 23, 2014, and U.S. Provisional Patent Application No. 62/159,678, filed May 11, 2015, the complete disclosures of which are incorporated herein by reference in their entireties for all purposes.

STATEMENT REGARDING FEDERALLY SPONSORED RESEARCH OR DEVELOPMENT

Not applicable

BACKGROUND

Field of the Invention

This invention relates generally to the field of exploration and production for hydrocarbons. More specifically, the invention relates to a method of pore type classification for petrophysical rock typing.

Background of the Invention

To optimize the production of hydrocarbon reserves from a subsurface formation or reservoir, petroleum engineers seek to understand the physical properties of these formations, including their porosity and permeability. For many geologic formations, their physical properties are determined primarily as they are deposited, and modified to some extent by pressure and heat. Therefore it is possible to describe and classify such geologic formations in terms of their depositional environments, with some acknowledgement of subsequent changes to the physical properties. By way of background, rock typing is a process of classifying reservoir rocks into distinct units, each of which was deposited under similar geological conditions and may have undergone similar diagenetic alterations. A given rock type, when accurately classified, is characterized by a unique permeability/porosity relationship, capillary pressure profile (or J function), and set of relative permeability curves. As a result, rock typing can lead to the estimation of formation permeability; and subsequently, the consistent and realistic simulation of reservoir dynamic behavior and production performance. In other words, proper rock typing may be used to accurately predict future or potential reservoir production through reservoir simulation methods, and may be used to make decisions as to where in a formation to drill certain wells or develop an existing hydrocarbon producing formation.

Much of the known reserves of oil and gas around the world are found in formations with complex pore systems (carbonates or unconventional reservoirs). This complexity is due to a combination of complex depositional rock fabric textures and diagenetic modification of the rocks. Post-depositional processes can modify the original petrophysical properties (e.g. permeability and irreducible water saturation) and result in a disconnection between original depositional rock fabric and current reservoir properties. However, a method has not yet been developed to describe the dominant pore type groups (PTGs) occurring within such a reservoir, and their associated petrophysical properties. These PTGs are determined independently of geological facies.

The shape of the mercury injection capillary pressure (MICP) curve reflects characteristics of a rock's porosity network, such as the distribution of pore and pore throat sizes, interconnectivity of the pores, and sorting of the pore throat sizes. Realizing that rocks of differing pore systems yield differently shaped capillary pressure curves, then representing the capillary pressure curve with a set of parameters that embodies these differences provides a means to easily group, or classify rocks according to unique combinations of these model parameters. Because the pore network governs the movement of fluids, the model can be used for saturation height analysis and permeability prediction.

Consequently, there is a need for methods and systems for pore type classification in petrophysical rock typing.

BRIEF SUMMARY

Embodiments of a method of pore type classification for petrophysical rock typing are disclosed herein. In general, embodiments of the method utilize parameterization of MICP data and/or other petrophysical data for pore type classification. Furthermore, embodiments of the method involve extrapolating, predicting, or propagating the pore type classification to the well log domain. The methods described here are unique in that: they describe the process from sample selection through log-scale prediction; PTGs are defined independently of the original depositional geology; parameters which describe the whole MICP curve shape can be utilized; and objective clustering can be used to remove subjective decisions. In addition, the method exploits the link between MICP data and the petrophysical characteristics of rock samples to derive self-consistent predictions of PTG, porosity, permeability and water saturation. Further details and advantages of various embodiments of the method are described in more detail below.

In an embodiment, a method of pore type classification comprises: a) selecting a plurality of core samples from a reservoir. The method also comprises b) using a mercury injection capillary pressure device to acquire one or more datasets from the plurality of core samples, the dataset comprising at least mercury injection capillary pressure (MICP) data, porosity, permeability, and grain density data. The method further comprises parameterizing, using a computer, the one or more datasets using a Gaussian error function and the mercury injection capillary pressure data to derive a plurality of curve fit parameters. In addition, the method comprises d) clustering, using the computer, the curve fit parameters to create one or more pore type groups. The method also comprises e) extrapolating the pore type groups to all of the core samples and f) propagating the pore type groups to a well log domain to classify a rock type from the reservoir, wherein the rock type is used to model the reservoir.

In an embodiment, a computer system comprises an interface for receiving one or more datasets, the datasets comprising at least mercury injection capillary pressure (MICP) data, porosity, permeability, and grain density data. The one or more datasets obtained from a plurality of samples taken from a subsurface reservoir. The computer system also comprises a memory resource. The computer system further comprises input and output functions for presenting and receiving communication signals to and from a human user. The computer system additionally comprises one or more central processing units for executing program instructions and program memory, coupled to the central processing unit, for storing a computer program including program instructions that, when executed by the one or more central processing units, cause the computer system to perform a plurality of operations for pore type classification. The operations comprise: a) parametrizing the one or more datasets using a Gaussian error function and a mercury injection capillary pressure dataset to derive a plurality of curve fit parameters. The operations also comprise b) clustering the curve fit parameters to create one or more pore type groups. In addition, the operations comprise c) extrapolating the pore type groups to all of the core samples and d) extrapolating the pore type groups to a well log domain to classify a rock type from the subsurface reservoir. The rock type can be used to model the subsurface reservoir.

In an embodiment, a non-transitory, computer readable medium having stored thereon instructions for pore type classification comprises machine executable code which when executed by at least one processor, causes the processor to perform steps comprising: a) parametrizing one or more datasets using a Gaussian error function and a mercury injection capillary pressure dataset to derive a plurality of curve fit parameters, the one or more datasets comprising at least mercury injection capillary pressure (MICP) data, porosity, permeability, and grain density data, the one or more datasets obtained from a plurality of samples from a subsurface reservoir. The steps also comprise b) clustering the curve fit parameters to create one or more pore type groups. In addition, the steps comprise c) extrapolating the pore type groups to all of the core samples and d) extrapolating the pore type groups to a well log domain to classify a rock type from the subsurface reservoir. The rock type can be used to model the subsurface reservoir.

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

NOTATION AND NOMENCLATURE

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ". Also, the term "couple" or "couples" is intended to mean either an indirect or direct connection. Thus, if a first device couples to a second device, that connection may be through a direct connection, or through an indirect connection via other devices and connections.

DETAILED DESCRIPTION OF THE PREFERRED EMBODIMENTS

Referring now to the Figures, embodiments of the disclosed methods will be described. As a threshold matter, embodiments of the methods may be implemented in numerous ways, as will be described in more detail below, including for example as a system (including a computer processing system), a method (including a computer implemented method), an apparatus, a computer readable medium, a computer program product, a graphical user interface, a web portal, or a data structure tangibly fixed in a computer readable memory. Several embodiments of the disclosed methods are discussed below. The appended drawings illustrate only typical embodiments of the disclosed methods and therefore are not to be considered limiting of its scope and breadth.

Embodiments of the disclosed methods may be used with the workflow and methods disclosed in U.S. patent application Ser. No. 13/347,512, which is incorporated herein in its entirety for all purposes.

Figure 1:
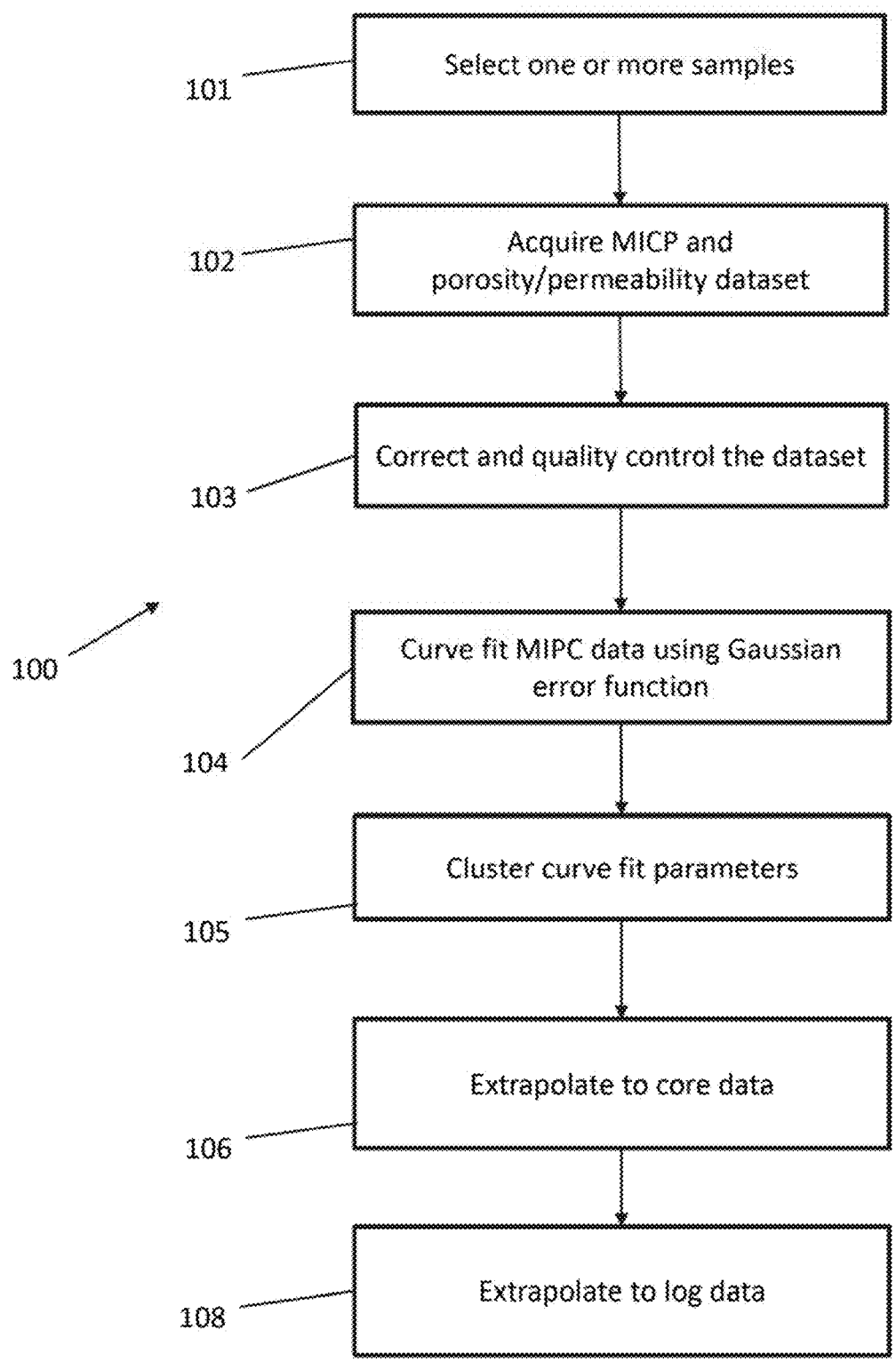
FIG. 1 illustrates an embodiment of a method for MICP-based pore typing.

FIG. 1 illustrates an embodiment of a method 100 for pore type classification. In the illustrated embodiment, the method 100 includes selecting a sample of cores from a reservoir in block 101. The method also includes using a mercury injection capillary pressure (MICP) measurement device to acquire one or more datasets from the plurality of core samples, the dataset comprising at least mercury injection capillary pressure, porosity, permeability, and grain density data in block 102. Any MICP measurement devices known to those of skill in the art may be used. However, other devices known to those skilled in the art may be used to acquire the datasets. The method also includes correction and quality control of the datasets in block 103 from the datasets obtained in 102. The method additionally may include parameterizing the one or more datasets (i.e. curve fitting the datasets) using a Gaussian error function and the mercury injection capillary pressure data to derive a plurality of curve fit parameters in block 104. Moreover, the method may include clustering the curve fit parameters to create one or more pore type groups (PTG) in block 105. The method also may include extrapolating the pore type groups to all of the core samples in block 106, and extrapolating the pore type groups to a well log domain in block 108. Each of these features will be described in detail below As mentioned above, embodiments of the method involve selecting one or more samples from a reservoir in 101. That is, sufficient and representative data is gathered from the subsurface formation. At this stage of an embodiment of the method there may not be a known link between geological processes and petrophysical properties, thus the reservoir may be statistically sampled in both geological and petrophysical space. This means that a statistically representative number of samples can be obtained from each depositional rock type. A statistically representative number of samples may be obtained from petrophysical (porosity-permeability) space. The sampling procedure can be optimized to meet both objectives in as few samples as possible.

In an embodiment, one way to measure if sufficient samples are collected may be by comparing two histograms of porosity which are made for a given depositional rock type showing all routine core analysis plugs acquired in one, and those selected for MICP analysis in the second, then both histograms should show similar values for mean and standard deviation. The same would be true for permeability, and for all depositional rock types identified.

Figure 2:
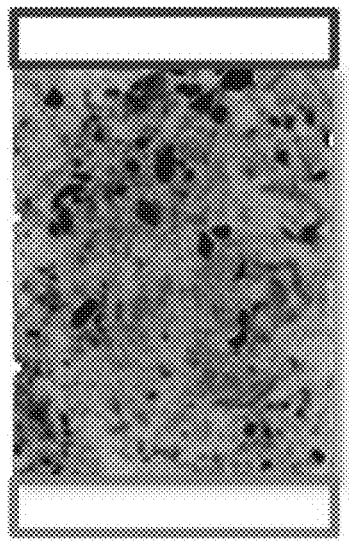
FIG. 2 illustrates how traditional methods use offcut trims for analysis such as MICP which may not be presentative of the whole core plug in heterogeneous reservoirs such as carbonates. Embodiments of the disclosed method proposes acquiring all data on the same bit of (smaller) rock volume to ensure equivalency of the various measurements.
Figure 2:
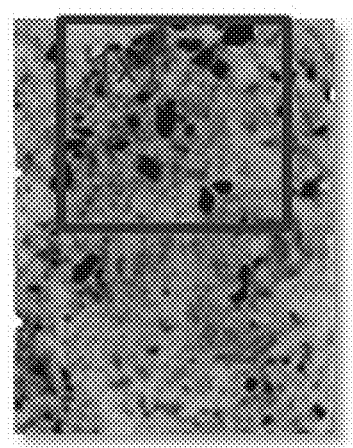

In another aspect of the method, core data can be acquired in 102. Most routine core analysis data is acquired using 1.5×2 inch core plugs and historically MICP data has been acquired on end trims from those plugs (FIG. 2). However, any suitable size core plugs may be used. For homogenous samples this may produce reasonable results, however for heterogeneous carbonates the end trim pore system may not be representative of the whole 1.5 inch diameter plug (see FIG. 2). For this process, smaller core plugs can be sub-cored from larger original plugs and all measurements for the analysis are performed on the same smaller core plug. While the measurements acquired can be extended, the core analysis may include, without limitation, the following procedures: a) Select plugs from RCA data set; b) Acquire plug computed tomography (CT) scan to identify heterogeneities, and identify suitable part of core for sub-coring; c) Sub-core to smaller (e.g. 1 in×1 in) plug; d) Undertake suitable cleaning (taking into account mineralogy, fluids and previous cleaning); e) Measure porosity, grain density and permeability using accepted American Petroleum Institute (API) techniques; f) undertake any other additional methods such as two dimensional nuclear magnetic resonance (2D-NMR); g) Undertake suitable cleaning if required to remove salts; h) MICP measurement (drainage or drainage+imbibition). Various steps may be substituted, subtracted or added in the above analysis procedure. In addition, such steps may be performed in any order.

Figure 3:
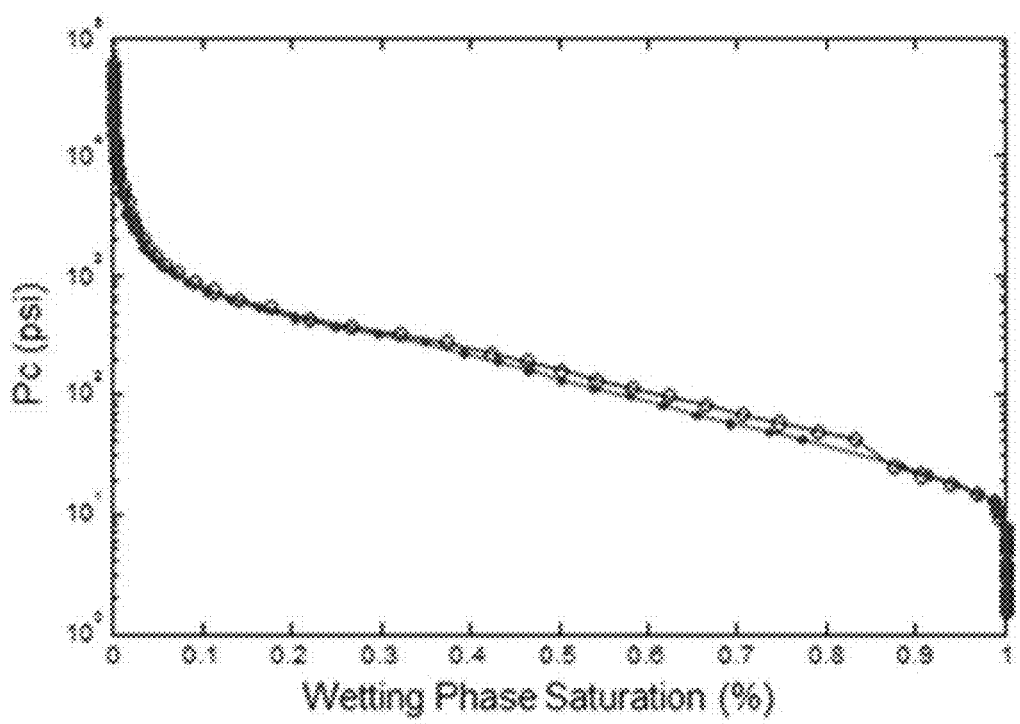
FIG. 3 illustrates examples of the application of some of the corrections that need to be applied to MICP data.
Figure 3:
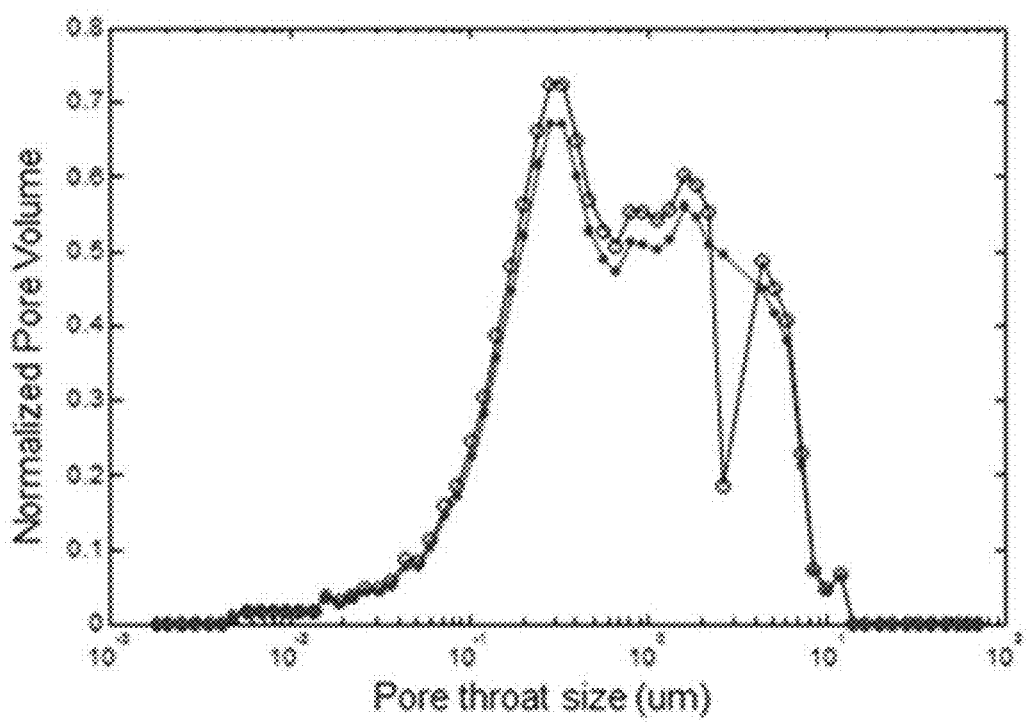

Referring back to FIG. 1, in an embodiment, the acquired data may be edited and corrected for quality control in 103. Data of poor or suspect quality may be filtered out and corrections made to good quality data where appropriate. Several corrections (while not always applicable) may be considered (see FIG. 3). In particular, examples of corrections may include without limitation: closure (conformance) corrections, merging of low and high pressure chamber data, adequate blank corrections (machine calibrations), interpolation replacement of bad data points, or combinations thereof. The following samples may be rejected where, without limitation, data where the signal to noise ratio is high enough to impact the quality of the optimization, data where the core plug porosity or permeability measurement failed, a sample where the difference between the core plug measured porosity and the MICP calculated porosity is greater than the defined tolerance (say 5-10% of the core plug porosity absolute value). Samples may also be rejected for other reasons known to those of skill in the art.

The accepted dataset (i.e. excluding any rejected samples) may be analyzed for appropriate sampling, as described above, to ensure that geological and petrophysical representativeness still holds true. For this reason, in embodiment, the method may use a more automated approach to sampling which lets the character of the existing data inform us about the number of samples required.

The existing routine core analysis (RCA) plugs may be used as the basis for making MICP sample selections. The underlying concept is that more samples from depositional rock types (DRTs) should be selected that exhibit poor correlation in Phi-K space, and less samples from DRTs that exhibit good correlation in Phi-K space. Likewise, more samples should be selected when there is a large range in porosity and/or permeability, and fewer samples for smaller ranges. To achieve this, for each DRT the RCA data can be gridded into a pre-defined number of porosity and permeability bins based on the range of all the available data. MICP samples can be selected from the center (or as close to as possible) of each of the grid cells that contain existing RCA data. Outliers can be excluded by limiting the sample selection to be from grid cells containing two or more samples and by looking at the content of neighboring cells. This method does not intend to capture the statistical frequency of samples in Phi-K space but the rather the heterogeneity of the dataset.

Figure 4:
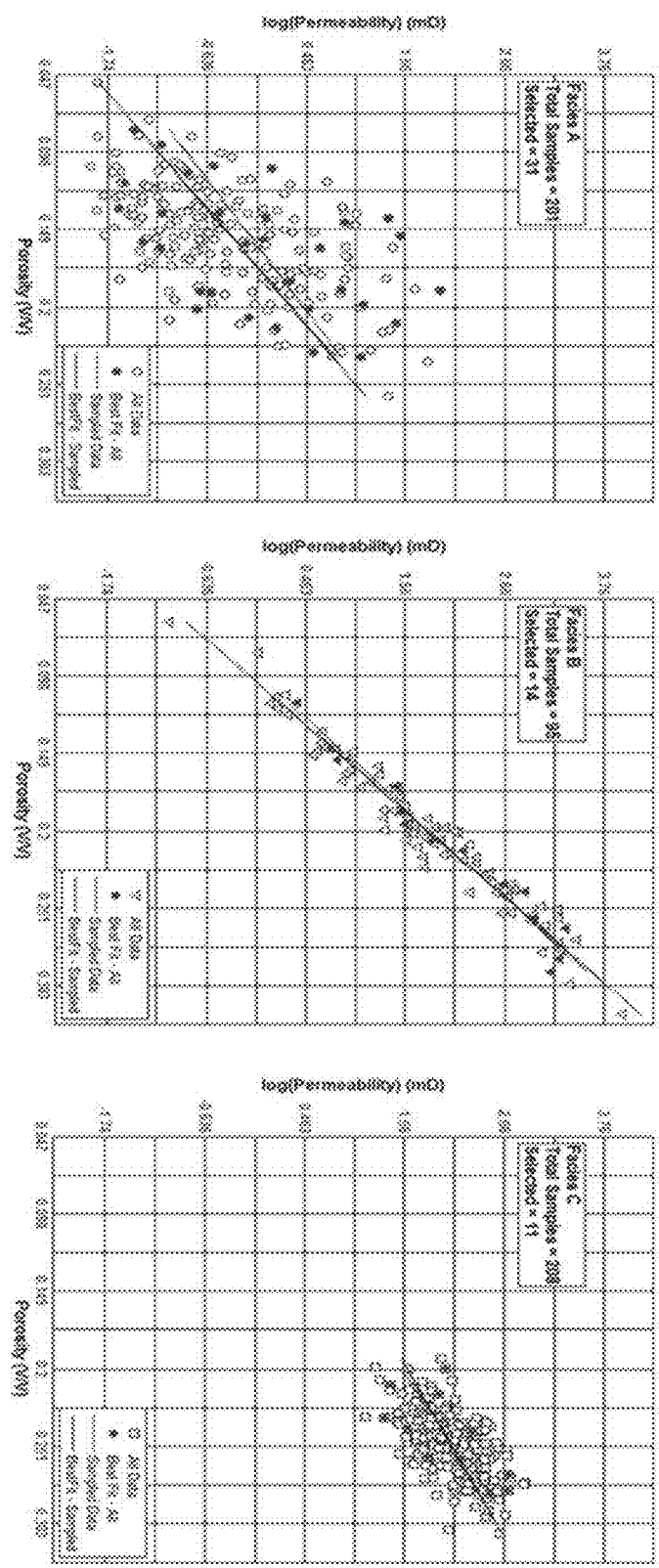
FIG. 4 illustrates the results of the automated sample selection applied to a synthetic data set consisting of three facies having different correlation and variation in porosity-permeability space. A sample is selected from each grid cell that contains two or more values in it. Open symbols are the original data, gray dots are the selected samples, black line os the regression from the original dataset and gray line regression from the selected sample set.

In FIG. 4 the sample selection method was applied to a synthetic dataset consisting of 3 depositional facies of varying correlation and variability. The number of samples selected from each facies was a function of the correlation of porosity and permeability and the variability of those properties. The total number of samples per facies or the frequency of samples within a given porosity/permeability range both appeared to have little impact.

In an embodiment, referring back to FIG. 1, the method also includes curve-fitting the MICP data using a Gaussian error function in 104. More particularly, embodiments of the method call for using a function to mathematically describe (mercury injection) capillary pressure measurements of rock samples having multi-modal pore systems. An inversion algorithm, driven by a modified Gaussian error forward model, composes a set of capillary pressure models characterizing respective pore modes into a cumulative capillary pressure model that approximates the measured capillary pressure data.

The goal is to model or parameterize, capillary pressure data in such a way as to translate the characteristics of the capillary pressure curve (and thus the characteristics of the pore network) into a few parameters that may be easily grouped into families of similar combinations of parameters.

An inversion algorithm may be used that decomposes (mercury injection) capillary pressure data into a set, or combination, of single pore mode models, where each pore mode model is uniquely described by three parameters. The inversion algorithm solves for the optimum combination of single pore mode models that, when combined, form a multimode model that fits the measured capillary pressure data. A least squares minimization of the objective function ($\varepsilon$), $$\varepsilon = \Sigma_{k=1}^{n}(S_{w_k} - \hat{S}_{w_k})^2 \quad (1)$$

is performed by varying the curve fitting parameters and the number of pore systems, where n=number of pressure measurements for a given sample, $S_{w_k}$ is the measured wetting phase saturation for a given pressure step k and $\hat{S}_{w_k}$ is the re-constructed wetting phase saturation for a given pressure step k.

In an embodiment, the formula to model a pore system can be a modified Gaussian error function and may be given by $$V_{P_c} = \frac{V_{P_\infty}}{2}\left(1 + \frac{2}{\sqrt{\pi}}\int_0^x e^{-t^2} \cdot dt\right) \quad (2)$$

where ($V_{P_c}$) is the intruded pore volume at a given capillary pressure ($P_c$) and $$x = \frac{1}{S}\log\left(\frac{P_c}{P_m}\right), \quad (3)$$

where S is the pore system shape factor, $P_m$ is the modal pressure of the pore system, and $V_{P_\infty}$ is the bulk volume of the pore system. $P_m$ is related to the pore throat size of the largest connected volume of pores, instead of the entry pore throat size.

Figure 5:
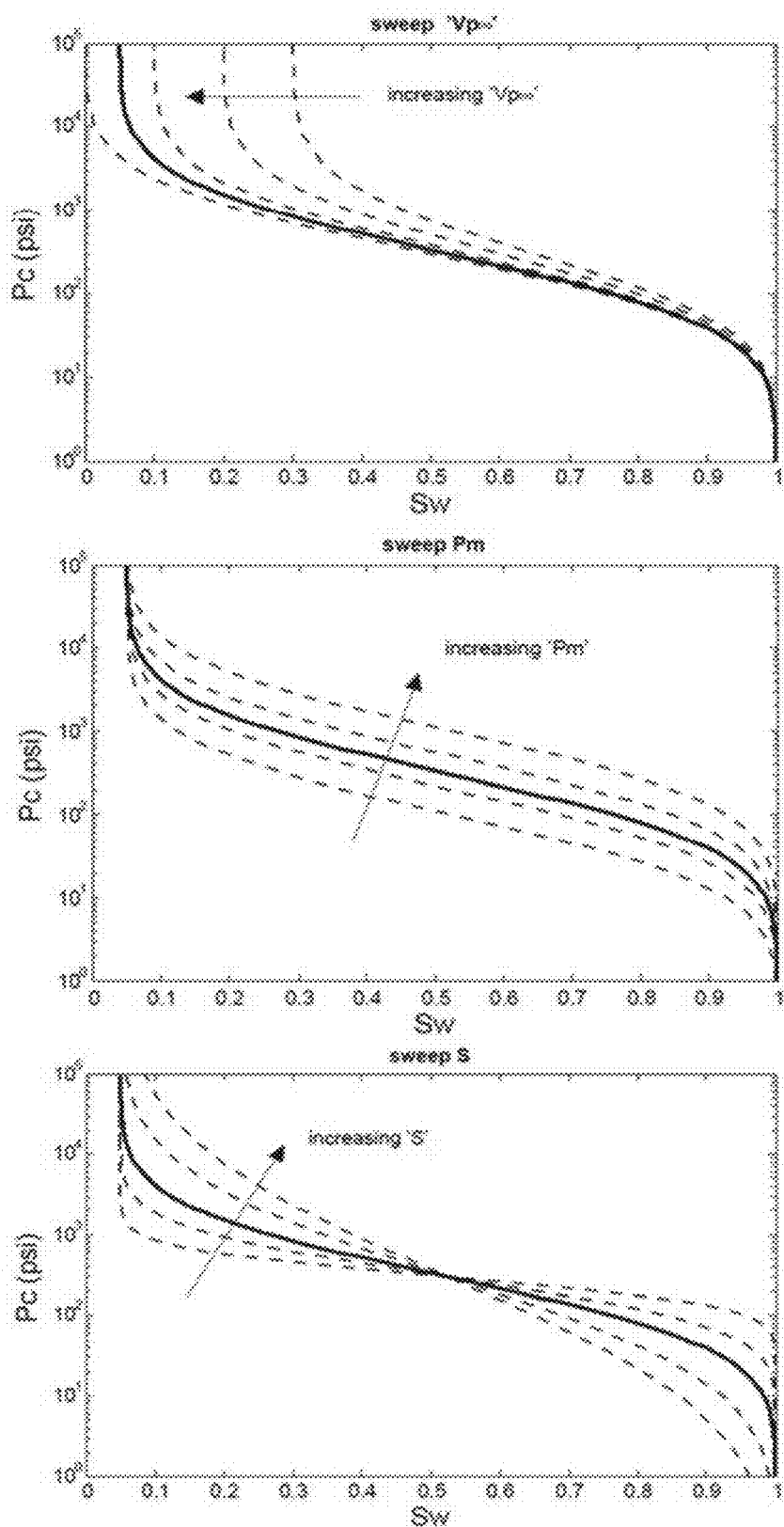
FIG. 5 illustrates the impact of varying the curve fitting parameters on the shape of the implemented Gaussian error function.

When more than one pore system is present in the formation, Equations 2 & 3 can be written in a more general form by summing the contribution of each individual system to the total pore volume, where p is the number of pore systems present, so that $$V_{P_T} = \sum_{i=1}^{p} \frac{V_{P_\infty(i)}}{2}\left(1 + \frac{2}{\sqrt{\pi}}\int_0^{x(i)} e^{-t^2} \cdot dt\right) \quad (4)$$

and, $$x(i) = \frac{1}{S_{(i)}}\log\left(\frac{P_c}{P_{m(i)}}\right). \quad (5)$$

and $V_{P_c}$ is the pore mode volume occupied by mercury at pressure $P_c$, $P_c$ is capillary pressure, $V_{P_\infty}$ is the pore mode volume occupied by mercury at infinite pressure, S is the pore system shape factor, and $P_m$ is the pore mode modal pressure. FIG. 5 shows the impact of varying the three curve fitting parameters individually. Varying $V_{P_\infty}$ will result in a change of the fraction of the total porosity occupied by that pore system. Varying $P_m$ can change the pressure at which the non-wetting phase will enter the pore system. Changing the S parameter changes the slope of the saturation curve or the width of the derivative curve. Thus the three optimized parameters are both practical in their relationship to observable characteristics of real MICP data.

Figure 8:
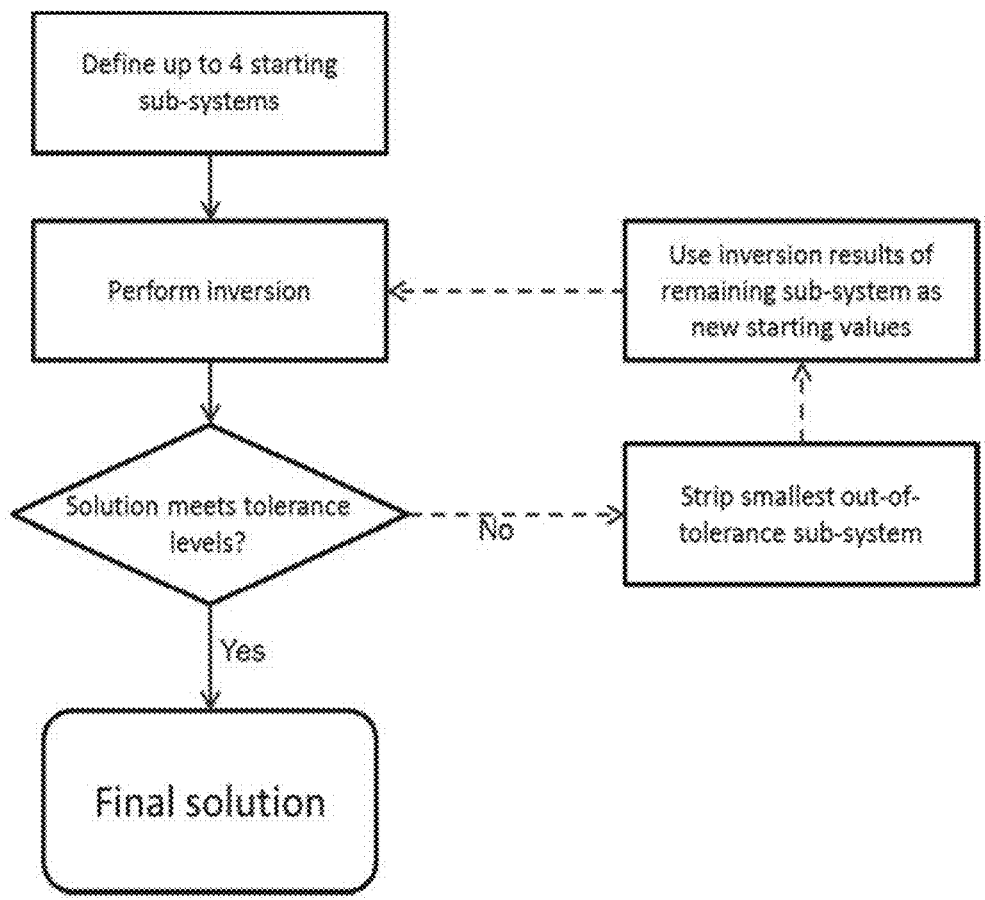
FIG. 8 illustrates a flow diagram showing an embodiment of the inversion process which may be used with embodiments of the disclosed method.

In an embodiment, the inversion process can include choosing an initial model with a large number of modes. An embodiment of the inversion process is shown in FIG. 8. For example the number of modes may be N=5. Although any number of modes may be selected. The inversion may then be executed and a solution with N modes may be obtained that minimizes the difference between the measured and predicted, or modeled, (mercury injection) capillary pressure data. If an individual mode does not satisfy an acceptance criteria (e.g. the pore mode volume is relatively small, and thus considered negligible), then this mode is stripped from the set, and the remaining modes from the solution form a new starting model with N=N−1 modes. The inversion may be repeated until a solution is obtained where all modes meet the acceptance criteria.

Figure 6:
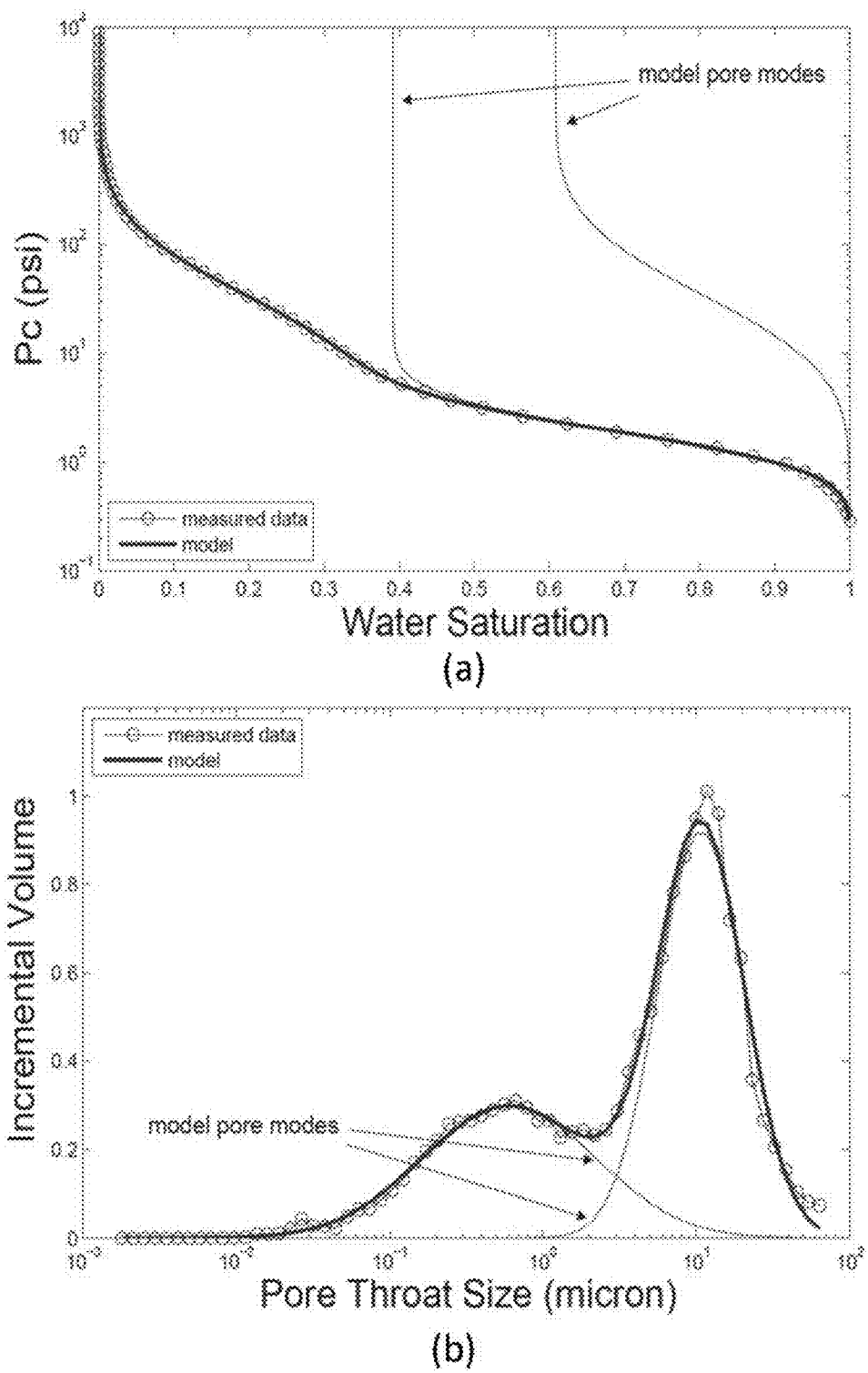
FIG. 6 illustrates an example of (a) mercury injection capillary pressure curve and (b) the derived pore throat size distribution showing the model fit to measured data using the new modified Gaussian error function. The models of the individual pore modes (blue lines) combine to form the final multimodal pore model (red line); These data are characteristic of a system with two dominant pore sizes (bimodal pore system)
Figure 7:
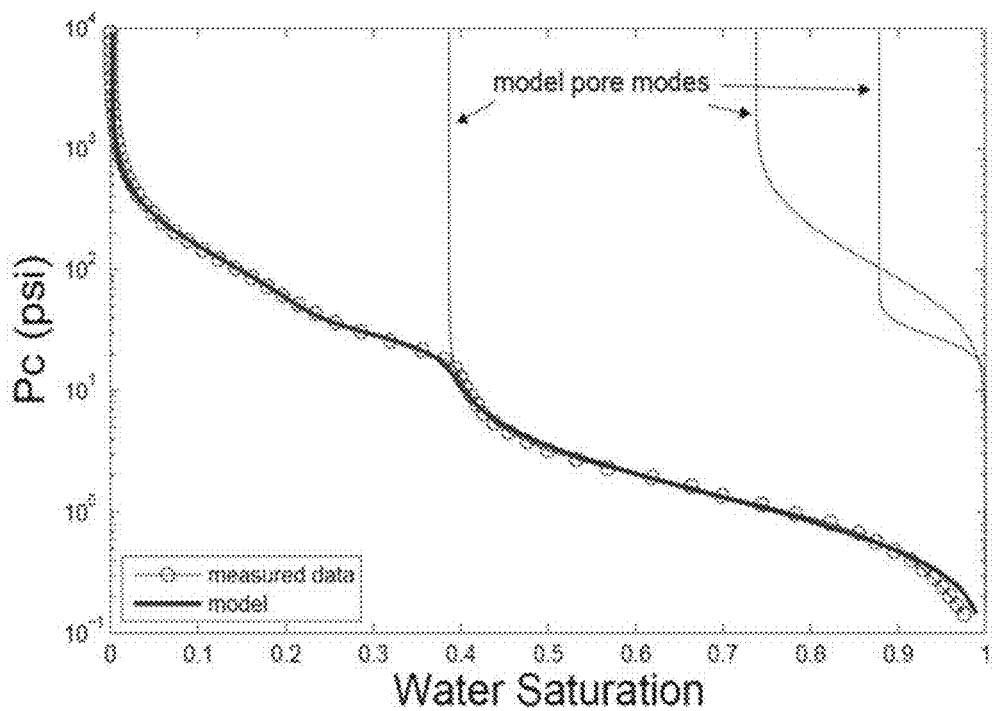
FIG. 7 illustrates an example of (a) mercury injection capillary pressure curve and (b) the derived pore throat size distribution showing the model fit to measured data using the new modified Gaussian error function. The models of the individual pore modes (blue lines) combine to form the final multimodal pore model (red line). These data are characteristic of a system with three dominant pore sizes (trimodal pore system)
Figure 7:
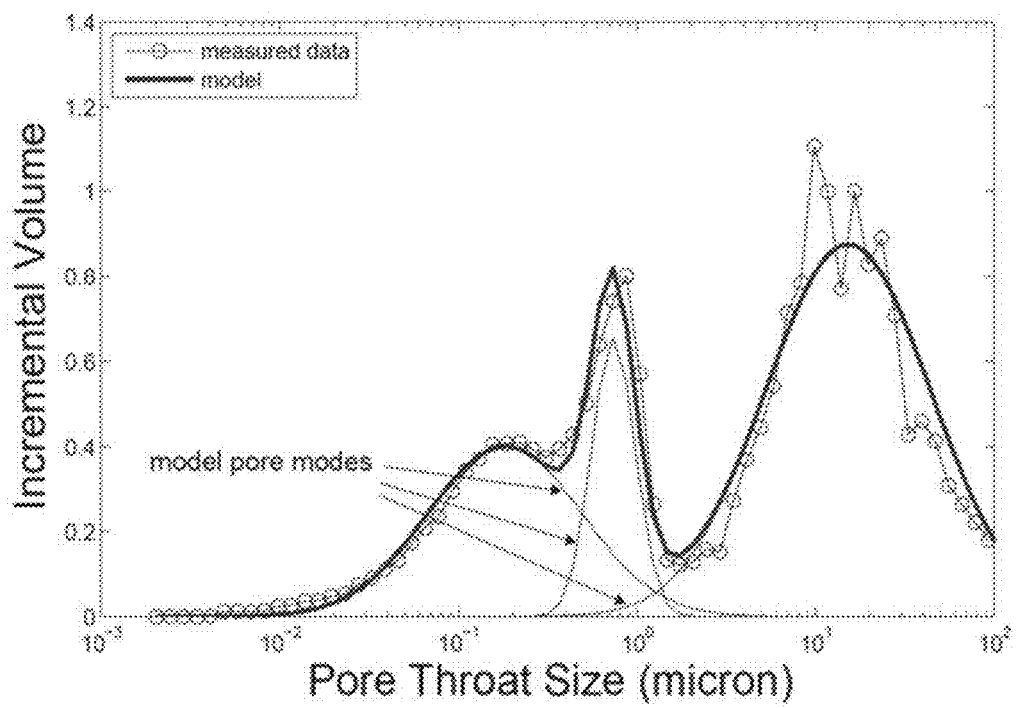

FIG. 6 and FIG. 7 present examples of the inversion applied to real mercury injection capillary pressure measurements conducted on carbonate rock samples. FIG. 6 and FIG. 7 show samples bearing characteristics of bimodal and trimodal pore systems, respectively. The plots labelled (a) in FIG. 6 and FIG. 7 show the measured and modeled capillary pressure curves, and the measured and modeled pore throat size distribution are shown in the plots labelled (b) in FIG. 6 and FIG. 7. These examples show excellent agreement between the measured data and the models predicted by the inversion.

The developed inversion algorithm provides fast and accurate quantification of pore networks of rock samples subjected to (mercury injection) capillary pressure measurements. This provides a means to accurately and efficiently compare large data sets, thus enabling the classification of many rock samples according to combinations of modeled parameters.

In an embodiment, referring back to FIG. 1, the method includes clustering the derived parameters to create pore type groups in 105. Once the parameters have been derived for all samples having MICP data, the curve fit parameters are used to cluster the samples into groups with similar pore type characteristics i.e. PTGs (see FIG. 9). The key clustering variables are the pore mode modal pressure $P_{mi}$, the pore mode volume $V_{pi}$ and the pore mode S value for each mode present in the sample, as well as the number of modes for a given sample. In an embodiment, the parameters can be selected from the two largest modes (which means clustering using 7 variables). The Multi-Resolution Graph-based (MRGC) clustering method can be used as it does not require the user to define the number of clusters, but rather identifies the number of clusters (at a given resolution) that are naturally present in the dataset.

Another aspect of embodiments of the method includes extrapolating MICP pore type groups to all core data in 106 of FIG. 1. With the final objective of log-propagation in mind, the objective is to increase the statistical base for log-domain training, by extrapolation of the PTGs to all available routine core data (FIG. 8). The assumptions made during this extrapolation step are that there is a singular relationship between porosity/permeability/grain density (PKG) and pore type group. This allows us to use the PKG values for each routine core analysis plug to estimate the associated pore type group. The method of K-nearest neighbor (KNN) propagation can be employed to perform the prediction as it is non-linear and does not rely on any statistical relations in the dataset. The MICP based PTGs may need to be optimized (i.e. some clusters may need to be merged) to enable core-based prediction, however PTG merging should be kept to a minimum at this stage. Some manual adjustment of extrapolated PTG may be required to remove outliers.

Figure 15:
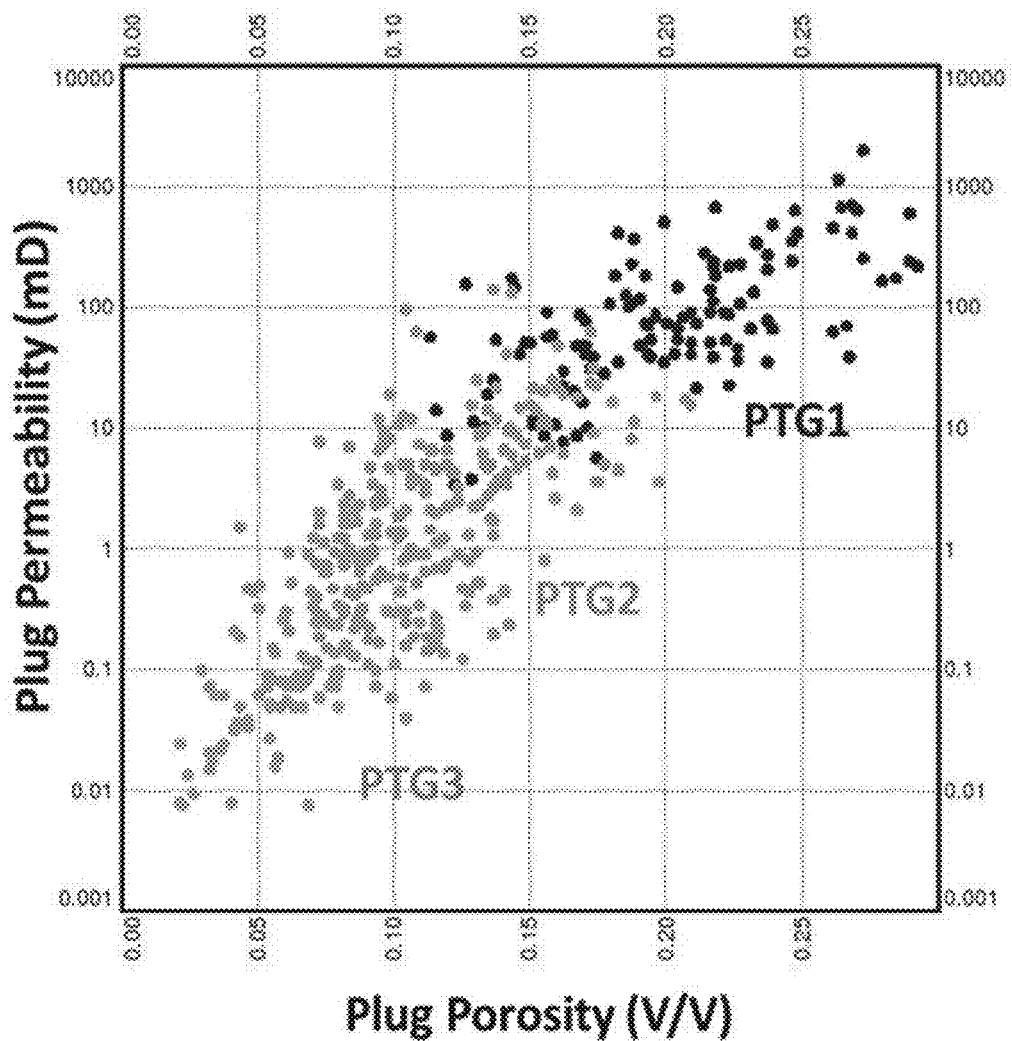
FIG. 15 illustrates a cross plot of permeability and porosity measurements, colored by the identified pore types based on the MICP data in the West Texas field. Pore types exhibit distinct ranges of porosity and permeability. Pore type 1 (PT1) has the highest porosity and permeability, while pore type 2 (PT2) and pore type 3 (PT3) have intermediate and low porosity and permeability, respectively.
Figure 16:
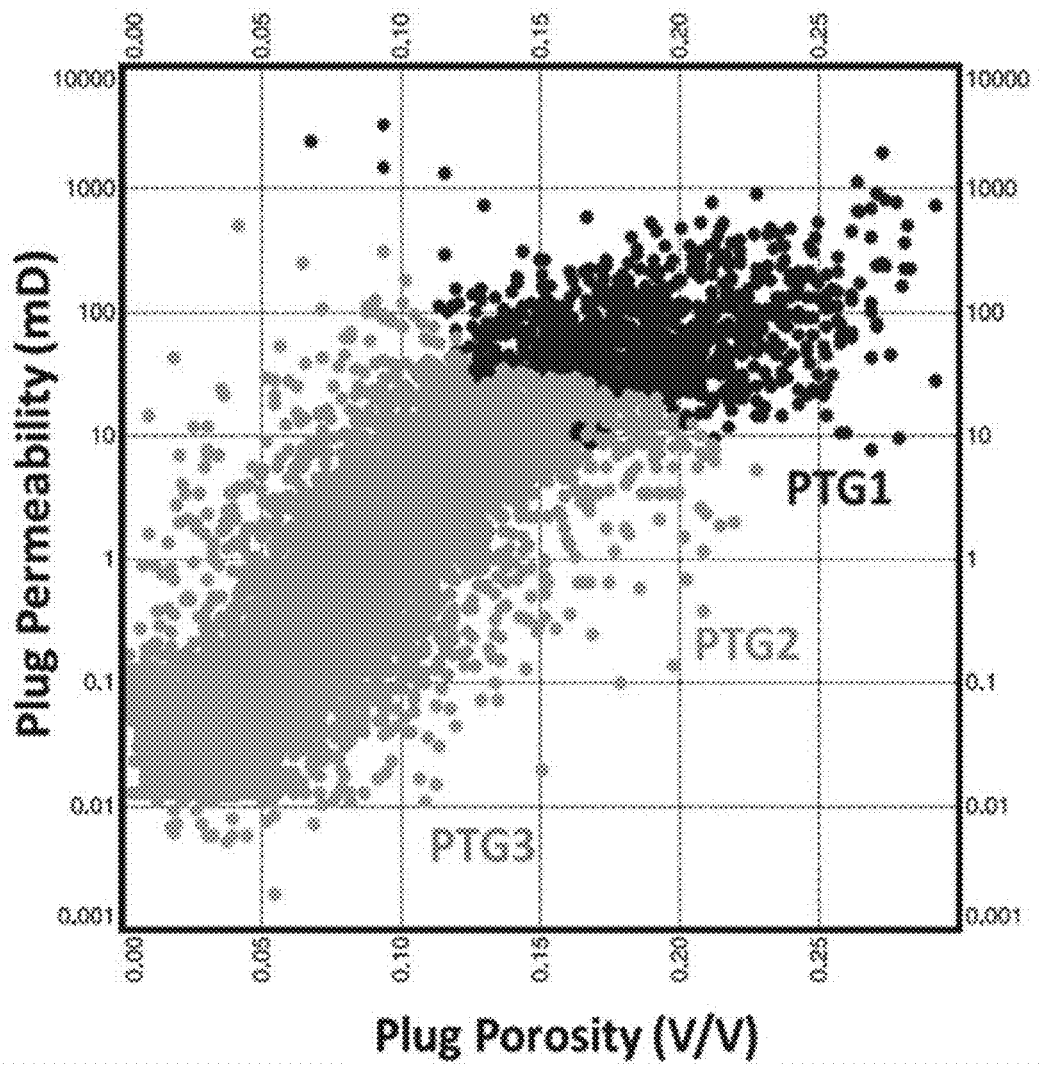
FIG. 16 illustrates a cross plot of permeability and porosity measurements, colored by the identified pore types after propagation of pore types to all routine core analysis plugs.

It has been found that when analyzed by depositional rock type there was little separation in porosity-permeability space. However, each of the MICP-PTGs occupy relatively unique space on the core plug porosity-permeability crossplot (FIG. 15). Core-PTGs were generated by making use of this separation in porosity-permeability space, assuming that for any given porosity-permeability pair there is a unique corresponding PTG. K-nearest neighbor (KNN) log prediction was used with an 80% prediction score to extrapolate the PTGs to the core domain (FIG. 16).

In further embodiments of the method, MICP pore type groups are predicted in the log domain in block 108 of FIG. 1. The set of core-extrapolated PTGs in combination with the optimum set of borehole log measurements or predicted curves can be used to build a training dataset for the purpose of PTG prediction in the log domain. The optimum set of log measurement/calculated curves may be generated using a statistical method that defines the best set of predictors for a given prediction (e.g. supervised diagnostics in Facimage™). The optimum set of log curves can be used to predict PTG for all relevant depths that have log coverage within the formation being investigated. The final set of PTGs to be predicted at the log-scale should be optimized for log prediction. Some of the core-based PTGs may need to be merged for the purpose of log prediction.

At the completion of the process, log-predicted PTGs based on clustering of parameterized MICP data (which is representative of the petrophysical and geological variation within the reservoir) are created. These log-based predictions are at the right scale to be integrated with other log-based geological information to generate petrophysical rock types as disclosed in U.S. patent application Ser. No. 13/347,512.

Having defined MICP-PTGs as the basis for propagation, petrophysical such as permeability and water saturation, properties can be calculated for each of the PTGs. These calculations can be made using averaged MICP data from each of the PTGs or a Monte-Carlo approach can be used to build probabilistic representations of the expected variability within each PTG. Both methods are described below.

In an embodiment of the method, the calibrated versions of these permeability models are used to predict petrophysical properties and select the model that works best for the reservoir under investigation. The permeability prediction with the highest r-squared for a given dataset can be selected.

Each PTG exhibits a range of petrophysical properties related to the variation in pore systems present. For each PTG, the number of pore systems and the properties of each pore system have been characterized, providing the information to synthetically re-create the observed variability with a Monte-Carlo approach. Each realization can generate a synthetic MICP curve based on the range of observed pore system parameters for a given PTG, and that MICP curve can be used to generate a calibrated permeability and an associated water saturation curve. Assuming that spatial variability of petrophysical properties within each PRT cannot be predicted, any 3D model can be populated in a way that preserves the PTG heterogenity observed at the core scale. Embodiments of the disclosed method also ensures internal consistency between the PTG, porosity, permeability and water saturation calculations.

Figure 11:
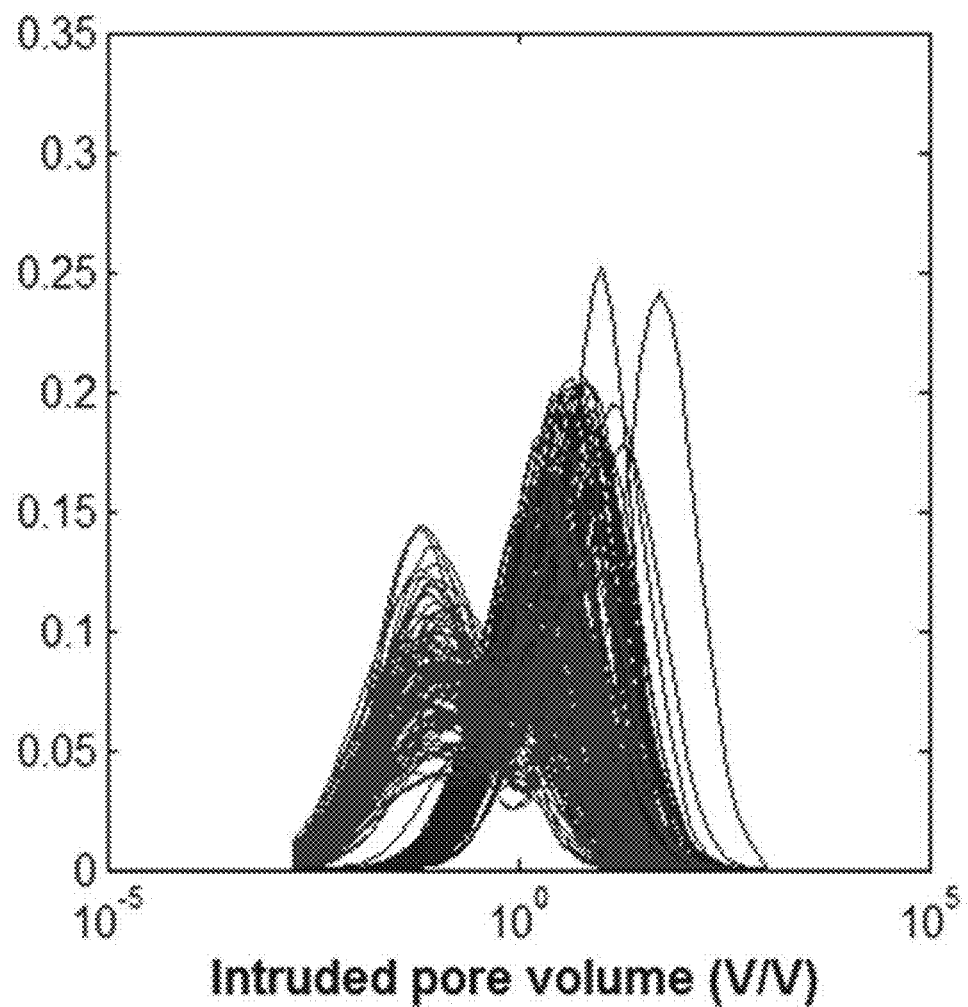
FIG. 11 illustrates a synthetically generated MICP derivative created using a Monte-Carlo process applied to a multi-modal modified Gaussian function using a distribution of fitting parameters.
Figure 12:
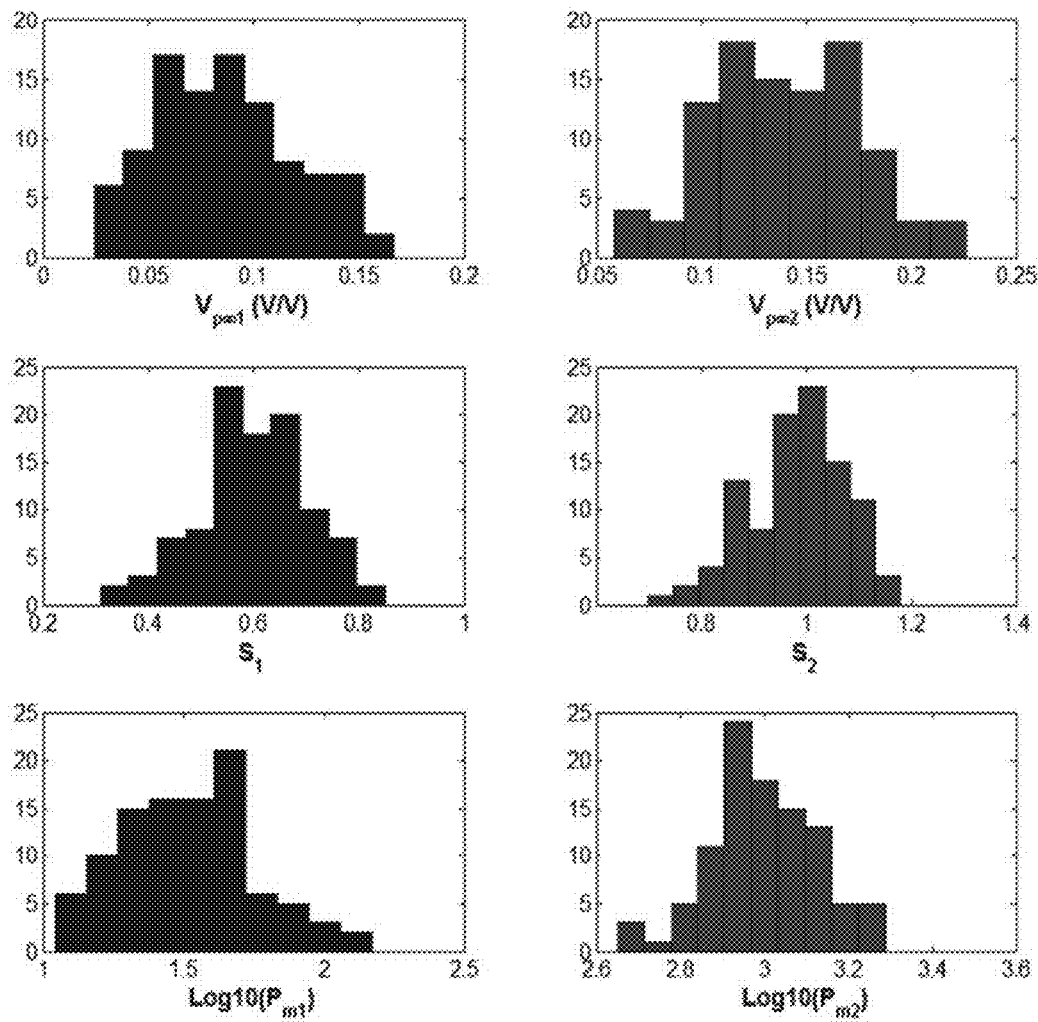
FIG. 12 illustrates distributions of MICP fitting parameters used to generate the synthetic data presented in FIG. 11.
Figure 13:
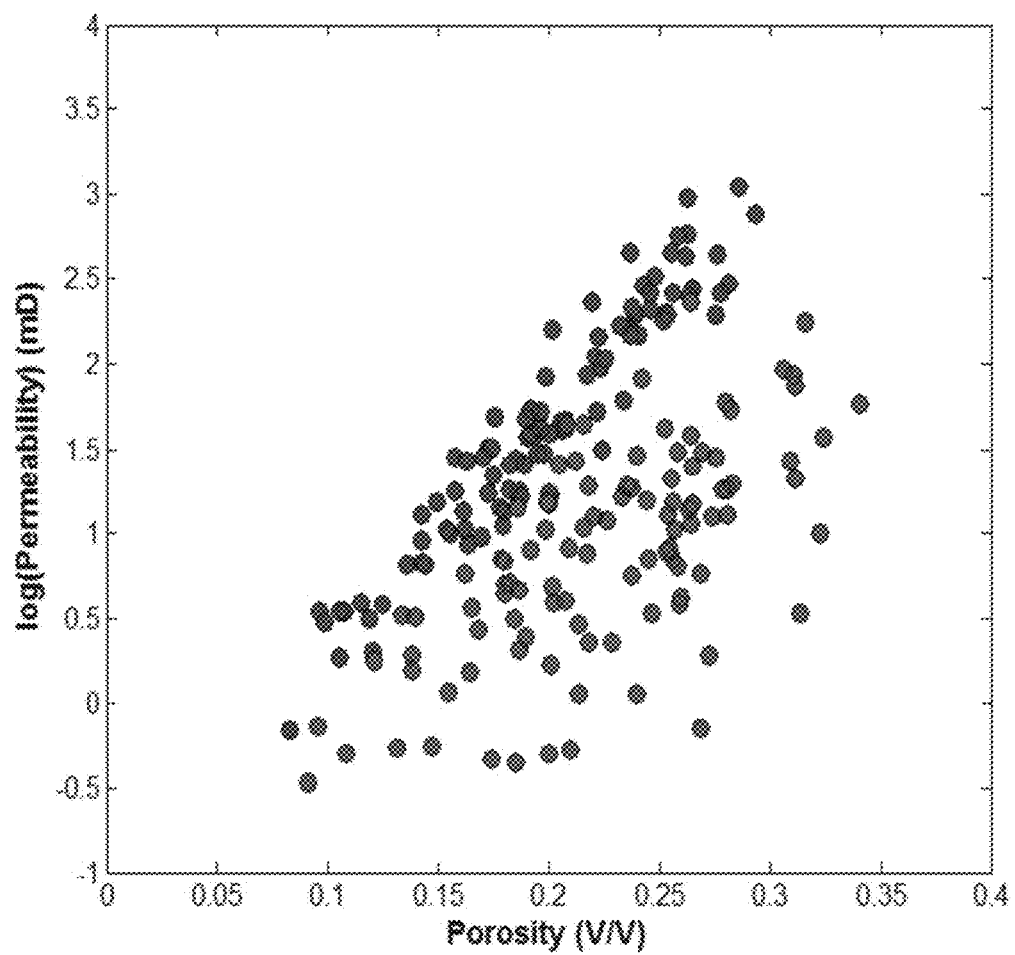
FIG. 13 illustrates porosity-permeability derived from the synthetic MICP data shown in FIG. 11 based on Winland R35 permeability estimates.

FIG. 11 shows an example of synthetically generated MICP curves. The data was produced using 100 realizations based on the distribution of curve fitting parameters shown in FIG. 12. The curve fitting parameter distributions are derived from actual MICP datasets and include any inherent cross-correlations in the parameters. FIG. 13 is the calculated permeability based on a calibrated Winland R35 method as is known in the art.

An alternative method for deriving PTG specific Sw-Ht functions may be to perform a global optimization of the curve fitting parameters with measured properties such as porosity and permeability. In this methodology, the curve-fitting parameters are defined as functions of porosity and/or permeability, $$Pm_{(i)} = a_{1i} + b_{1i} \log(k) + c_{1i} \varphi$$

$$V_{p\infty_{(i)}} = a_{2i} + b_{2i} \log(k) + c_{2i} \varphi$$

$$S_{(i)} = a_{3i} + b_{3i} \log(k) + c_{3i} \varphi \quad (1)$$

where $a_1$, $a_2$, $a_3$, $b_1$, $b_2$, $b_3$, $C_1$, $c_2$ and $c_3$ are regression fitting parameters globally optimized to build the $S_w$-$H_t$ function for each PTG. Ultimately, $S_w$ can be described as a function of capillary pressure (or height above free water level), porosity and permeability.

Although carbonate formations may have been emphasized throughout this disclosure, it is noted that embodiments of the method may be used with any rock types known to those of skill in the art. The results of the disclosed method (e.g. rock classification) can be used in reservoir modeling and simulation of a certain subsurface formation or hydrocarbon producing reservoir. Reservoir modeling is the final step in the reservoir-characterization process, and consists of building an upscaled geologic model for input to the fluid-flow numerical simulator. Dynamic reservoir simulation is used to forecast ultimate hydrocarbon recovery on the basis of a given production scheme, or to compare the economics of different recovery methods. Based on the results of reservoir simulation or modeling, decision can ultimately be made on selecting a recovery method, making an economic decision whether or not to drill in a specific area, and also to make estimates of hydrocarbons in a reservoir.

Those skilled in the art will appreciate that the disclosed methods may be practiced using any one or combination of hardware and software configurations, including but not limited to a system having single and/or multi-processor computer processors system, hand-held devices, programmable consumer electronics, mini-computers, mainframe computers, supercomputers, and the like. The disclosed methods may also be practiced in distributed computing environments where tasks are performed by servers or other processing devices that are linked through one or more data communications networks. In a distributed computing environment, program modules may be located in both local and remote computer storage media including memory storage devices.

Figure 17:
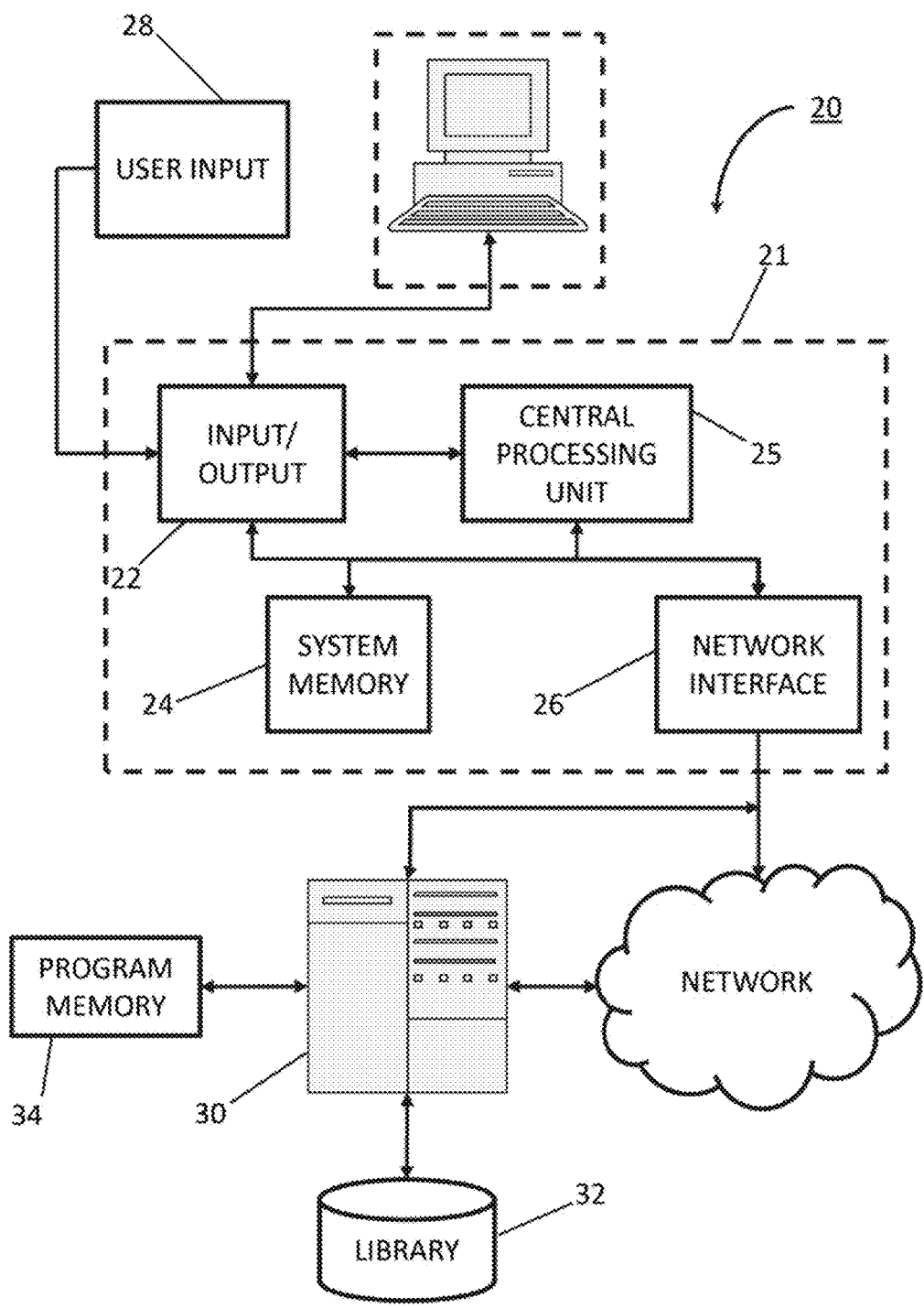
FIG. 17 illustrates a schematic of a system which may be used in conjunction with embodiments of the disclosed methods.

FIG. 17 illustrates, according to an example of an embodiment computer system 20, which may be used to for the disclosed methods of pore type classification. In this example, system 20 is as realized by way of a computer system including workstation 21 connected to server 30 by way of a network. Of course, the particular architecture and construction of a computer system useful in connection with this invention can vary widely. For example, system 20 may be realized by a single physical computer, such as a conventional workstation or personal computer, or alternatively by a computer system implemented in a distributed manner over multiple physical computers. Accordingly, the generalized architecture illustrated in FIG. 17 is provided merely by way of example.

Figure 9:
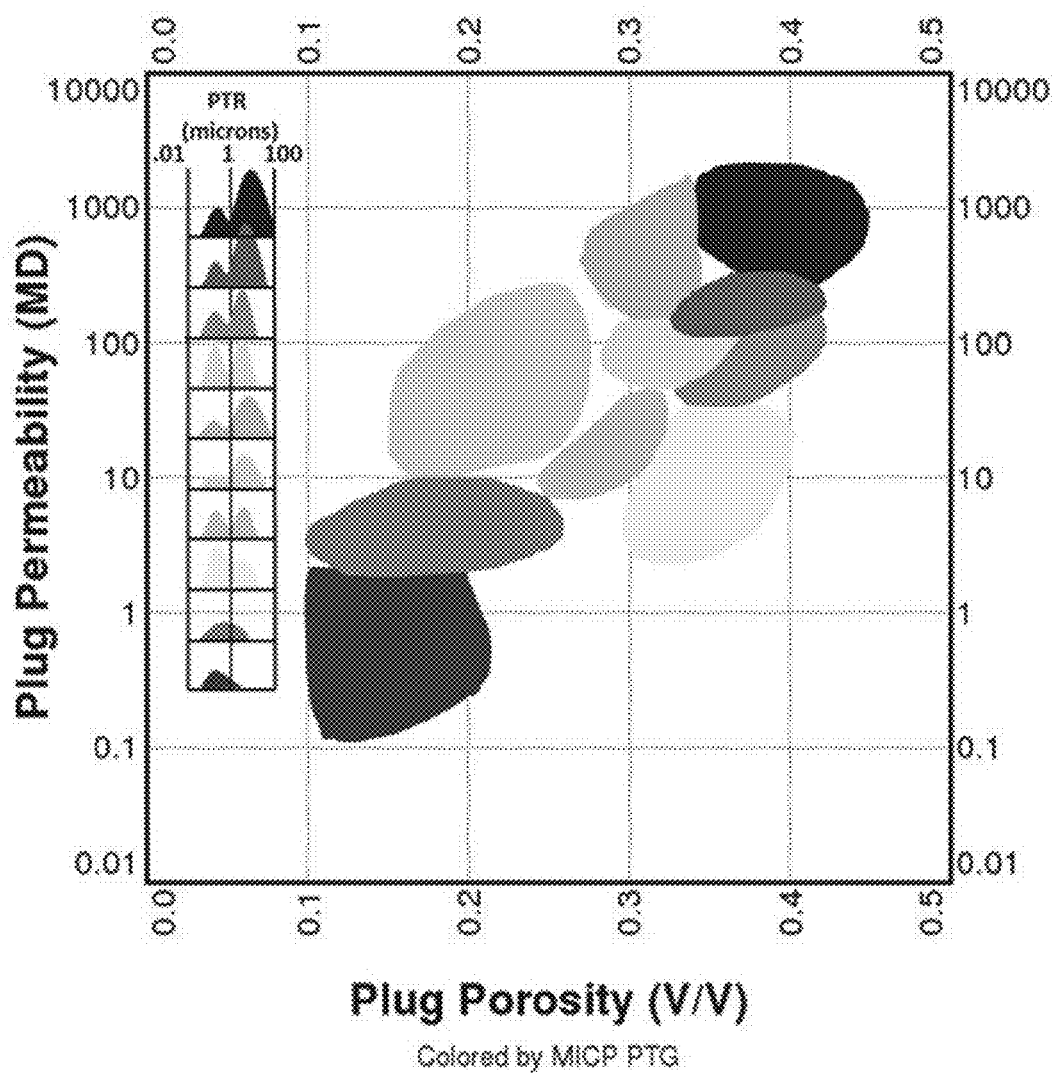
FIG. 9 illustrates an example of porosity permeability data colored by pore type groups derived from clustering of MICP parameters. The inset shows the MICP pore throat radius (PTR) derivative shape that is typical of the PTG for the interpreted dataset.

As shown in FIG. 17 and as mentioned above, system 20 may include workstation 21 and server 30. Workstation 21 includes central processing unit 25, coupled to system bus. Also coupled to system bus is input/output interface 22, which refers to those interface resources by way of which peripheral functions P (e.g., keyboard, mouse, display, etc.) interface with the other constituents of workstation 21. Central processing unit 25 refers to the data processing capability of workstation 21, and as such may be implemented by one or more CPU cores, co-processing circuitry, and the like. The particular construction and capability of central processing unit 25 is selected according to the application needs of workstation 21, such needs including, at a minimum, the carrying out of the functions described in this specification, and also including such other functions as may be executed by computer system. In the architecture of allocation system 20 according to this example, system memory 24 is coupled to system bus, and provides memory resources of the desired type useful as data memory for storing input data and the results of processing executed by central processing unit 25, as well as program memory for storing the computer instructions to be executed by central processing unit 25 in carrying out those functions. Of course, this memory arrangement is only an example, it being understood that system memory 24 may implement such data memory and program memory in separate physical memory resources, or distributed in whole or in part outside of workstation 21. In addition, as shown in FIG. 9, data inputs 28 may be input via input/output function 22, and stored in a memory resource accessible to workstation 21, either locally or via network interface 26.

Network interface 26 of workstation 21 is a conventional interface or adapter by way of which workstation 21 accesses network resources on a network. As shown in FIG. 17, the network resources to which workstation 21 has access via network interface 26 includes server 30, which resides on a local area network, or a wide-area network such as an intranet, a virtual private network, or over the Internet, and which is accessible to workstation 21 by way of one of those network arrangements and by corresponding wired or wireless (or both) communication facilities. In this embodiment of the invention, server 30 is a computer system, of a conventional architecture similar, in a general sense, to that of workstation 21, and as such includes one or more central processing units, system buses, and memory resources, network interface functions, and the like. According to this embodiment of the invention, server 30 is coupled to program memory 34, which is a computer-readable medium that stores executable computer program instructions, according to which the operations described in this specification are carried out by allocation system 30. In this embodiment of the invention, these computer program instructions are executed by server 30, for example in the form of a "web-based" application, upon input data communicated from workstation 21, to create output data and results that are communicated to workstation 21 for display or output by peripherals P in a form useful to the human user of workstation 21. In addition, library 32 is also available to server 30 (and perhaps workstation 21 over the local area or wide area network), and stores such archival or reference information as may be useful in allocation system 20. Library 32 may reside on another local area network, or alternatively be accessible via the Internet or some other wide area network. It is contemplated that library 32 may also be accessible to other associated computers in the overall network.

The particular memory resource or location at which the measurements, library 32, and program memory 34 physically reside can be implemented in various locations accessible to allocation system 20. For example, these data and program instructions may be stored in local memory resources within workstation 21, within server 30, or in network-accessible memory resources to these functions. In addition, each of these data and program memory resources can itself be distributed among multiple locations. It is contemplated that those skilled in the art will be readily able to implement the storage and retrieval of the applicable measurements, models, and other information useful in connection with this embodiment of the invention, in a suitable manner for each particular application.

According to this embodiment, by way of example, system memory 24 and program memory 34 store computer instructions executable by central processing unit 25 and server 30, respectively, to carry out the disclosed operations described in this specification, for example, by way of which the operations for pore type classification may be performed. These computer instructions may be in the form of one or more executable programs, or in the form of source code or higher-level code from which one or more executable programs are derived, assembled, interpreted or compiled. Any one of a number of computer languages or protocols may be used, depending on the manner in which the desired operations are to be carried out. For example, these computer instructions may be written in a conventional high level language, either as a conventional linear computer program or arranged for execution in an object-oriented manner. These instructions may also be embedded within a higher-level application. Such computer-executable instructions may include programs, routines, objects, components, data structures, and computer software technologies that can be used to perform particular tasks and process abstract data types. It will be appreciated that the scope and underlying principles of the disclosed methods are not limited to any particular computer software technology. For example, an executable web-based application can reside at program memory 34, accessible to server 30 and client computer systems such as workstation 21, receive inputs from the client system in the form of a spreadsheet, execute algorithms modules at a web server, and provide output to the client system in some convenient display or printed form. It is contemplated that those skilled in the art having reference to this description will be readily able to realize, without undue experimentation, this embodiment of the invention in a suitable manner for the desired installations. Alternatively, these computer-executable software instructions may be resident elsewhere on the local area network or wide area network, or downloadable from higher-level servers or locations, by way of encoded information on an electromagnetic carrier signal via some network interface or input/output device. The computer-executable software instructions may have originally been stored on a removable or other non-volatile computer-readable storage medium (e.g., a DVD disk, flash memory, or the like), or downloadable as encoded information on an electromagnetic carrier signal, in the form of a software package from which the computer-executable software instructions were installed by allocation system 20 in the conventional manner for software installation.

To further illustrate various illustrative embodiments of the disclosed methods, the following examples are provided.

EXAMPLE

An embodiment of the disclosed methods was applied to an existing dataset from a field in West Texas and its outcome was validated using the available dynamic data.

An extensive database of 850 MICP measurements (plug trim offcut samples) from 62 wells were available as the basis for MICP pore typing in the West Texas field. After careful quality control 501 were accepted (59%) due to excess porosity difference greater than 3 porosity units or due to lack of a permeability measurement.

Figure 14:
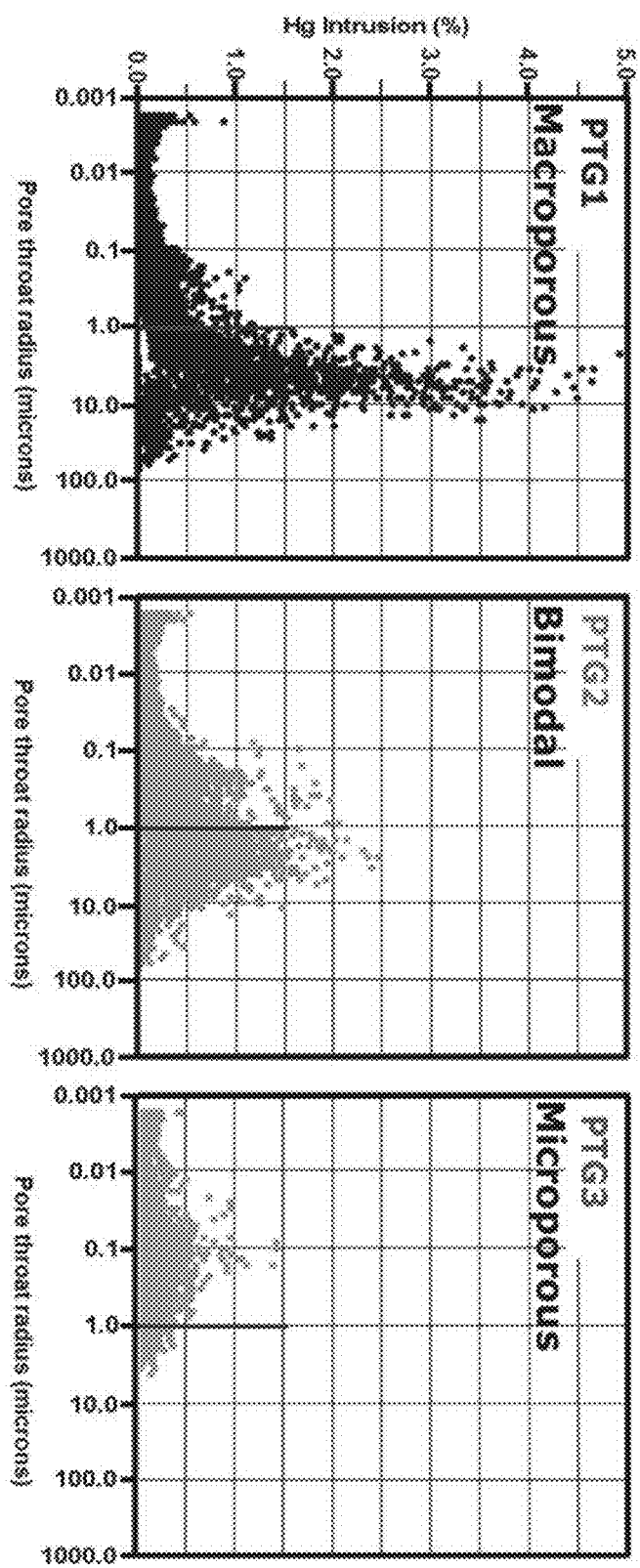
FIG. 14 illustrates results for the mercury intrusion vs pore-throat radius for the three identified pore types in the West Texas field. PTG1 is dominantly macro-porous, samples in PTG2 exhibit strong bimodality, while samples in PTG3 are dominantly micro-porous and generally have low total porosity.

MICP measurements were characterized by fitting the multi-modal Gaussian function into each sample measurement. Clustering (and subsequent lumping) of the MICP parameters of the two pore sub-systems produced three main MICP-PTGs (FIG. 14)—PTG1 (highest porosity and dominated by macro-pores), PTG2 (bimodal pores), and PTG3 (low porosity and dominated by micro-pores).

It has been found that when analyzed by depositional rock type there was little separation in porosity-permeability space. However, each of the MICP-PTGs occupy relatively unique space on the core plug porosity-permeability crossplot (FIG. 15). Core-PTGs were generated by making use of this separation in porosity-permeability space, assuming that for any given porosity-permeability pair there is a unique corresponding PTG. KNN log prediction was used with an 80% prediction score to extrapolate the PTGs to the core domain (FIG. 16).

Figure 10:
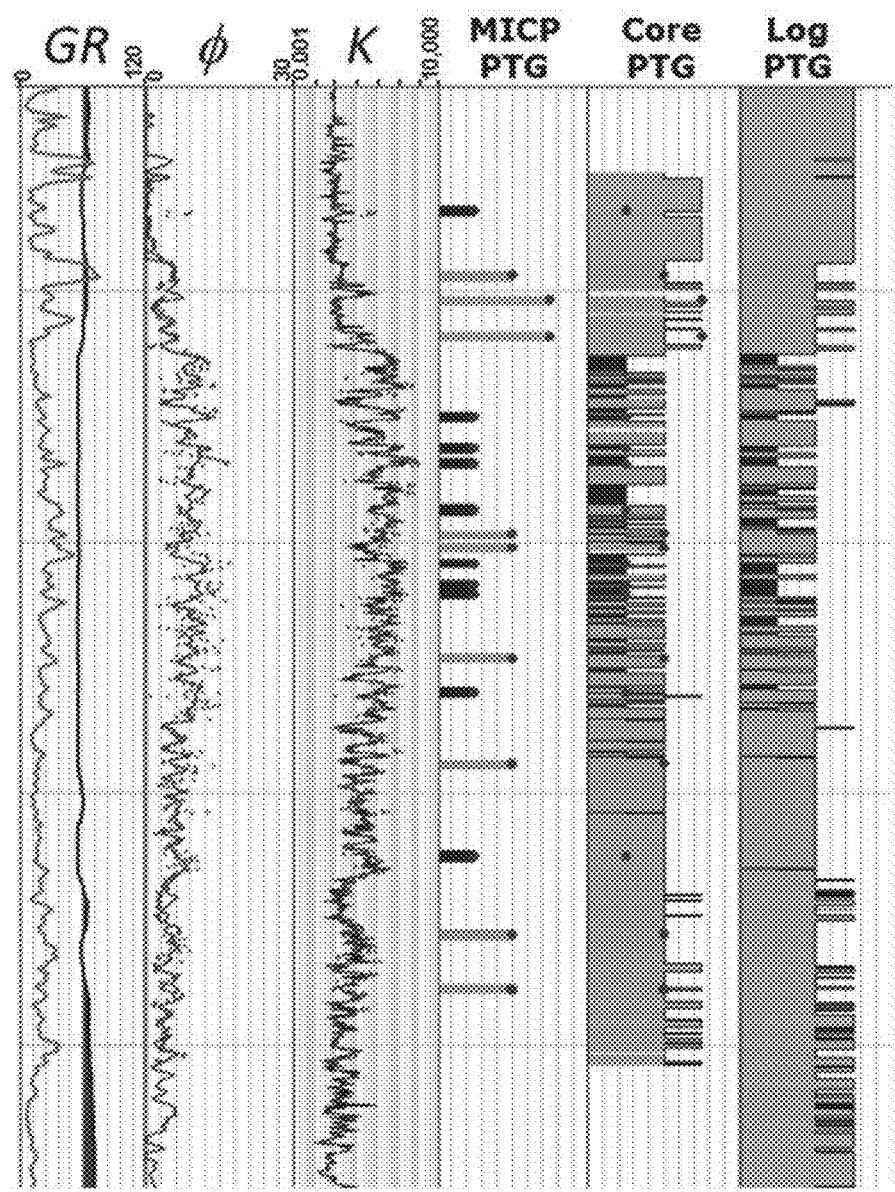
FIG. 10 illustrates a depth plot which shows that significant increase in data is observed when MICP pore types are extrapolated to all core plugs with porosity/permeability/grain density (PKG) measurements.

Following the core extrapolation process the PTG database had 7,400 samples which were used a basis for log propagation (FIG. 10). The eight best log predictors were used to build a K-nearest neighbor (KNN) log prediction model to generate log-PTGs away from the cored intervals. The best predictor logs were picked by comparing prediction scores for all combinations of a selected list of 15 measured and interpreted logs. The logs selected for prediction were: illite volume, gamma-ray, bulk density, neutron porosity, compressional slowness, shallow resistivity, photoelectric factor, and neutron-density separation.

The quality of the log prediction of PTG was cross-validated using a blind dataset which comprised 20% of the original dataset and showed a 73% prediction score.

While the embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

The discussion of a reference is not an admission that it is prior art to the present invention, especially any reference that may have a publication date after the priority date of this application. The disclosures of all patents, patent applications, and publications cited herein are hereby incorporated herein by reference in their entirety, to the extent that they provide exemplary, procedural, or other details supplementary to those set forth herein.

What is claimed is:

1. A method of pore type classification, the method comprising:
a) selecting a plurality of core plugs from a reservoir;
b) acquiring a dataset from the plurality of core plugs, wherein the dataset comprises mercury injection capillary pressure (MICP) data, porosity, permeability, and grain density data for each core plug of the plurality of core plugs, and wherein a MICP device houses each core plug of the plurality of core plugs in order to acquire the MICP data for the core plug;
c) parameterizing, using a computer, the dataset using a Gaussian error function and the MICP data to derive a plurality of curve fit parameters, wherein the Gaussian error function comprises a formula comprising:

$$V_{P_c} = \frac{V_{P_\infty}}{2}\left(1 + \frac{2}{\sqrt{\pi}} \int_0^x e^{-t^2} \cdot dt\right)$$

where $V_{P_c}$ is pore volume at a given capillary pressure and $$x = \frac{1}{S}\log\left(\frac{P_c}{P_m}\right),$$

where S is a pore system shape factor, $P_m$ is a modal pressure of the pore system, and $V_{P_\infty}$ is a bulk volume of the pore system;
d) clustering, using the computer, the plurality of curve fit parameters to create one or more pore type groups for the plurality of core plugs with the MICP data;
e) extrapolating the one or more pore type groups to a different plurality of core plugs without any MICP data; and f) propagating the one or more pore type groups of the plurality of core plugs with the MICP data and the different plurality of core plugs without any MICP data to a well log domain to classify a rock type from the reservoir, wherein the rock type is used to model the reservoir.

2. The method of claim 1, further comprising correcting and performing quality control on the dataset.

3. The method of claim 1, wherein the plurality of core plugs represents a statistically representative number of samples for a depositional rock type.

4. The method of claim 1, wherein the plurality of core plugs represents a statistically representative number of samples from a petrophysical space.

5. The method of claim 1, wherein (c) further comprises:
   c1) choosing an initial model with a number of modes, N, wherein N is an integer;
   c2) executing a solution with the N number of modes to minimize a difference between the MICP data and predicted MICP data generated by the Gaussian error function;
   c3) if an individual mode of the N number of modes does not satisfy an acceptance criteria, then this mode is removed from the N number of modes, and remaining modes of the N number of modes from the solution form a new starting model with N=N−1 modes;
   c4) repeating (c2) and (c3) until a final solution is obtained where all modes meet the acceptance criteria.

6. The method of claim 1, wherein (b) further comprises, for each core plug of the plurality of core plugs:
   b1) acquiring plug computed tomography (CT) scan to identify heterogeneities, and identify suitable part of the core plug for sub-coring;
   b2) sub-coring the core plug based on b1) to a plug size capable of being housed in the MICP device;
   b3) measuring the porosity, the grain density, and the permeability of the core plug using accepted American Petroleum Institute (API) techniques; and
   b4) acquiring the MICP data of the core plug.

7. The method of claim 6, wherein the plug size is 1 inch×1 inch.

8. The method of claim 1, wherein the reservoir comprises a carbonate formation.

9. The method of claim 1, further comprising calculating one or more petrophysical properties for each of the one or more pore type groups.

10. The method of claim 9, wherein the calculating the one or more petrophysical properties for each of the one or more pore type groups comprises using a Monte-Carlo approach to determine one or more probabilistic representations within each of the one or more pore type groups and using the one or more probabilistic representations to calculate the one or more petrophysical properties.

11. The method of claim 9, wherein calculating the one or more petrophysical properties for each of the one or more pore type groups comprises using averaged MICP data from each of the one or more pore type groups.

12. The method of claim 11, further comprising, for each of the one or more pore type groups, generating a MICP synthetic curve based on a range of observed pore system parameters, and using the MICP synthetic curve to generate a calibrated permeability and an associated water curve.

13. A system comprising:
   an interface for receiving a dataset for a plurality of core plugs from a reservoir, wherein the dataset comprises mercury injection capillary pressure (MICP) data, porosity, permeability, and grain density data for each core plug of the plurality of core plugs, and wherein a MICP data is acquired using a MICP device that houses each core plug of the plurality of core plugs in order to acquire the MICP data for the core plug;
   a memory resource;
   input and output functions for presenting and receiving communication signals to and from a human user;
   one or more central processing units for executing program instructions; and program memory, coupled to the one or more central processing units, for storing a computer program including program instructions that, when executed by the one or more central processing units, cause the computer system to perform a plurality of operations for pore type classification, the operations comprising:
   a) parametrizing the dataset using a Gaussian error function and the MICP data to derive a plurality of curve fit parameters, wherein the Gaussian error function comprises a formula comprising:

$$V_{P_c} = \frac{V_{P_\infty}}{2}\left(1 + \frac{2}{\sqrt{\pi}} \int_0^x e^{-t^2} \cdot dt\right)$$

where $V_{P_c}$ is pore volume at a given capillary pressure and $$x = \frac{1}{S}\log\left(\frac{P_c}{P_m}\right),$$

where S is a pore system shape factor, $P_m$ is a modal pressure of the pore system, and $V_{P_\infty}$ is a bulk volume of the pore system;
   b) clustering the plurality of curve fit parameters to create one or more pore type groups for the plurality of core plugs with the MICP data;
   c) extrapolating the one or more pore type groups to a different plurality of core plugs without any MICP data; and
   d) extrapolating the one or more pore type groups of the plurality of core plugs with the MICP data and the different plurality of core plugs without any MICP data to a well log domain to classify a rock type from the reservoir, wherein the rock type is used to model the reservoir.

14. The system of claim 13, wherein (a) further comprises:
   a1) choosing an initial model with a number of modes, N, wherein N is an integer;
   a2) executing a solution with the N number of modes to minimize a difference between the MICP data and predicted MICP data generated by the Gaussian error function;
   a3) if an individual mode of the N number of modes does not satisfy an acceptance criteria, then this mode is removed from the N number of modes, and remaining modes of the N number of modes from the solution form a new starting model with N=N-1 modes;
   a4) repeating a2) and a3) until a final solution is obtained where all modes meet the acceptance criteria.

15. The system of claim 13, further comprising the MICP device to acquire the MICP data.

16. The system of claim 13, wherein, for each core plug of the plurality of core plugs:

plug computed tomography (CT) scan is acquired to identify heterogeneities, and identify suitable part of the core plug for sub-coring;

sub-coring the core plug based on b 1) to a plug size capable of being housed in the MICP device is performed;

the porosity, the grain density, and the permeability of the core plug is measured using accepted American Petroleum Institute (API) techniques; and the MICP data of the core plug is performed.

17. A non-transitory, computer readable medium having stored thereon instructions for pore type classification comprising machine executable code which when executed by at least one processor, causes the at least one processor to perform steps comprising:

a) parametrizing a dataset for a plurality of core plugs from a reservoir using a Gaussian error function and mercury injection capillary pressure (MICP) data to derive a plurality of curve fit parameters, wherein the dataset comprises the MICP data, porosity, permeability, and grain density data for each core plug of the plurality of core plugs, wherein the MICP data is acquired using a MICP device that houses each core plug of the plurality of core plugs in order to acquire the MICP data for the core plug, wherein the Gaussian error function comprises a formula comprising:

$$V_{P_c} = \frac{V_{P_\infty}}{2}\left(1 + \frac{2}{\sqrt{\pi}}\int_0^x e^{-t^2} \cdot dt\right)$$

where $V_{P_c}$ is pore volume at a given capillary pressure and $$x = \frac{1}{S}\log\left(\frac{P_c}{P_m}\right),$$

where S is a pore system shape factor, $P_m$ is a modal pressure of the pore system, and $V_{P_\infty}$ is a bulk volume of the pore system;

b) clustering the plurality of curve fit parameters to create one or more pore type groups for the plurality of core plugs with the MICP data;

c) extrapolating the one or more pore type groups to a different plurality of core plugs without any MICP data; and d) extrapolating the one or more pore type groups of the plurality of core plugs with the MICP data and the different plurality of core plugs without any MICP data to a well log domain to classify a rock type from the subsurface reservoir, wherein the rock type is used to model the subsurface reservoir.

18. The non-transitory, computer readable medium of claim 17, wherein (a) further comprises:

a1) choosing an initial model with a number of modes, N, wherein N is an integer;

a2) executing a solution with the N number of modes to minimize a difference between the MICP data and predicted MICP data generated by the Gaussian error function;

a3) if an individual mode of the N number of modes does not satisfy an acceptance criteria, then this mode is removed from the N number of modes, and remaining modes of the N number of modes from the solution form a new starting model with N=N−1 modes;

a4) repeating a2) and a3) until a final solution is obtained where all modes meet the acceptance criteria.

* * * * *